US011364205B2

(12) United States Patent
Ortenzi et al.

(10) Patent No.: US 11,364,205 B2
(45) Date of Patent: Jun. 21, 2022

(54) STABLE LOW DIGESTIVE ENZYME CONTENT FORMULATION

(75) Inventors: Giovanni Ortenzi, Monza (IT); Giuseppe De Franza, Pessano con Bornago (IT); Danilo Clementi, Seriate (IT); Christian Stollberg, Carugate (IT); Luigi Boltri, Agrate Brianza (IT)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 13/251,926

(22) Filed: Oct. 3, 2011

(65) Prior Publication Data

US 2012/0201875 A1    Aug. 9, 2012

Related U.S. Application Data

(60) Provisional application No. 61/389,037, filed on Oct. 1, 2010.

(51) Int. Cl.
*A61K 9/20* (2006.01)
*A61K 38/46* (2006.01)
*A61K 9/28* (2006.01)
*A61K 9/48* (2006.01)

(52) U.S. Cl.
CPC .......... *A61K 9/2054* (2013.01); *A61K 9/2072* (2013.01); *A61K 9/2866* (2013.01); *A61K 9/4808* (2013.01); *A61K 38/465* (2013.01)

(58) Field of Classification Search
USPC .......................................... 424/451, 94, 463
See application file for complete search history.

(56) References Cited

U.S. PATENT DOCUMENTS

| | | |
|---|---|---|
| 2,751,330 A | 9/1956 | Reichert |
| 3,844,891 A | 10/1974 | Hess et al. |
| 4,079,125 A | 3/1978 | Sipos |
| 4,237,229 A | 12/1980 | Hartdegen et al. |
| 4,280,971 A | 7/1981 | Wischniewski et al. |
| 4,447,412 A | 5/1984 | Bilton |
| 4,623,624 A | 11/1986 | Schultze |
| 4,704,295 A | 11/1987 | Porter et al. |
| 4,786,505 A | 11/1988 | Lovgren et al. |
| 4,849,227 A | 7/1989 | Cho |
| 4,859,471 A | 8/1989 | Fulberth et al. |
| 5,075,231 A | 12/1991 | Moreau et al. |
| 5,225,202 A | 7/1993 | Hodges et al. |
| 5,260,074 A | 11/1993 | Sipos |
| 5,306,506 A | 4/1994 | Zema et al. |
| 5,308,832 A | 5/1994 | Garleb et al. |
| 5,324,514 A | 6/1994 | Sipos |
| 5,378,462 A | 1/1995 | Boedecker et al. |
| 5,460,812 A | 10/1995 | Sipos |
| 5,570,104 A | 10/1996 | Hayashi |
| 5,578,304 A * | 11/1996 | Sipos ..................... 424/94.1 |
| 5,665,428 A | 9/1997 | Cha et al. |
| 5,733,575 A | 3/1998 | Mehra et al. |
| 5,733,763 A | 3/1998 | Markussen et al. |
| 5,750,104 A | 5/1998 | Sipos |
| 5,861,177 A | 1/1999 | Atzl et al. |
| 5,861,291 A | 1/1999 | Abboudi et al. |
| 6,051,220 A | 4/2000 | Scharpe |
| 6,313,102 B1 | 11/2001 | Colaco et al. |
| 6,318,650 B1 | 11/2001 | Breitenbach et al. |
| 6,352,974 B1 | 3/2002 | Ghirri et al. |
| 6,426,091 B1 | 7/2002 | Okumura et al. |
| 6,607,747 B2 | 8/2003 | Ullah et al. |
| 6,855,336 B2 | 2/2005 | Chen et al. |
| 6,955,903 B2 | 10/2005 | Kulkarni et al. |
| 7,201,923 B1 | 4/2007 | van Lengerich |
| 7,658,918 B1 | 2/2010 | Ortenzi et al. |
| 8,071,089 B2 | 12/2011 | Schuler et al. |
| 8,221,747 B2 | 7/2012 | Ortenzi et al. |
| 8,246,950 B2 | 8/2012 | Ortenzi et al. |
| 8,293,229 B2 | 10/2012 | Ortenzi et al. |
| 8,562,978 B2 | 10/2013 | Ortenzi et al. |
| 8,562,979 B2 | 10/2013 | Ortenzi et al. |

(Continued)

FOREIGN PATENT DOCUMENTS

| | | |
|---|---|---|
| AU | 2011309763 B2 | 8/2015 |
| CA | 2263703 A1 | 8/1999 |

(Continued)

OTHER PUBLICATIONS

Hasegawa, Microcrystalline Cellulose Grade 12 versus Classic Grade 102, Pharmaceutical Technology Europe 13 (11), 28-34, 2001.*
US Pharmacopeia, Chapter 786, Particle Size Distribution Estimation by Analytical Sieving, Web download, Jun. 26, 2009.*
Avicel-FMC, Avicel product sheet, FMC Biopolymer, 2012.*
Gohel, A review of co-processed directly compressible excipients, J. Pharm. Pharmaceutical Sciences, 8(1):76-93, 2005.*
Avicel-FMC, Avicel product sheet, Apr. 22, 2010.*
International Search Report for PCT/IB2011/002419, dated Jun. 2, 2012.
Written Opinion for PCT/IB2011/002419, dated Jun. 2, 2012.
Eurasian Office Action (with English translation), dated Jan. 30, 2015, corresponding to Eurasian Application No. 201390409/28; 4 total pages.

(Continued)

*Primary Examiner* — Louise W Humphrey
*Assistant Examiner* — Srikanth Patury
(74) *Attorney, Agent, or Firm* — K&L Gates LLP

(57) ABSTRACT

The present invention is directed to a pharmaceutical composition or dosage form having a stable, low (diluted) digestive enzyme content comprising at least one digestive enzyme and at least one carrier, or a dosage form thereof. The invention is also directed to a process of preparation of the composition or the dosage form. In addition the invention is directed to the treatment and prevention of disorders or conditions associated with a digestive enzyme deficiency in a patient in need thereof, comprising administering to said patient a pharmaceutically acceptable amount of the composition having a stable low digestive enzyme content or dosage form thereof.

27 Claims, 1 Drawing Sheet

(56) References Cited

U.S. PATENT DOCUMENTS

| | | |
|---|---|---|
| 8,562,980 B2 | 10/2013 | Ortenzi et al. |
| 8,562,981 B2 | 10/2013 | Ortenzi et al. |
| 8,784,884 B2 | 7/2014 | Perrett et al. |
| 2001/0024660 A1 | 9/2001 | Ullah et al. |
| 2001/0046493 A1 | 11/2001 | Margolin et al. |
| 2002/0044968 A1 | 4/2002 | van Lengerich |
| 2002/0054907 A1 | 5/2002 | Devane et al. |
| 2002/0187536 A1 | 12/2002 | Kulkarni et al. |
| 2004/0057944 A1 | 3/2004 | Galle et al. |
| 2004/0101562 A1 | 5/2004 | Maio |
| 2004/0121010 A1 | 6/2004 | Hirsh et al. |
| 2004/0197321 A1* | 10/2004 | Sipos et al. ............... 424/94.2 |
| 2004/0213847 A1 | 10/2004 | Matharu et al. |
| 2005/0019417 A1 | 1/2005 | Ko et al. |
| 2005/0158299 A1 | 7/2005 | Margolin et al. |
| 2005/0208133 A1 | 9/2005 | Tsutsumi et al. |
| 2005/0281876 A1 | 12/2005 | Li et al. |
| 2006/0121017 A1 | 6/2006 | Margolin et al. |
| 2006/0198838 A1 | 9/2006 | Fallon |
| 2007/0025977 A1* | 2/2007 | Mulberg ..................... 424/94.6 |
| 2007/0141151 A1 | 6/2007 | Silver et al. |
| 2007/0148151 A1 | 6/2007 | Frink et al. |
| 2007/0148152 A1 | 6/2007 | Shlieout et al. |
| 2007/0190142 A1 | 8/2007 | Breitenbach et al. |
| 2008/0187525 A1 | 8/2008 | Porubcan |
| 2008/0199448 A1 | 8/2008 | Ross et al. |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0299185 A1 | 12/2008 | Ortenzi et al. |
| 2009/0081184 A1 | 3/2009 | Margolin et al. |
| 2009/0117180 A1* | 5/2009 | Ortenzi et al. ............ 424/463 |
| 2009/0148545 A1 | 6/2009 | Falk et al. |
| 2009/0226414 A1 | 9/2009 | Tijssen et al. |
| 2009/0232789 A1 | 9/2009 | Fallon |
| 2010/0021537 A1 | 1/2010 | Ortenzi et al. |
| 2010/0239559 A1 | 9/2010 | Freedman et al. |
| 2010/0270183 A1 | 10/2010 | Ortenzi et al. |
| 2011/0064799 A1* | 3/2011 | Perrett et al. ............ 424/452 |
| 2011/0123605 A1 | 5/2011 | Ortenzi et al. |
| 2011/0123633 A1 | 5/2011 | Ortenzi et al. |
| 2011/0123634 A1 | 5/2011 | Ortenzi et al. |
| 2012/0177629 A1 | 7/2012 | Broussard et al. |
| 2012/0201875 A1 | 8/2012 | Ortenzi et al. |
| 2013/0251926 A1 | 9/2013 | Wood et al. |
| 2014/0170212 A1 | 6/2014 | Ortenzi et al. |
| 2014/0287035 A1 | 9/2014 | Perrett et al. |
| 2014/0295474 A1 | 10/2014 | Latino et al. |

FOREIGN PATENT DOCUMENTS

| | | | |
|---|---|---|---|
| CA | 2419572 A1 | 8/2004 | |
| CN | 87103560 A | 5/1988 | |
| CN | 1235824 A | 11/1999 | |
| CN | 1376519 A | 10/2002 | |
| CN | 1489476 A | 4/2004 | |
| CN | 101249081 A | 8/2008 | |
| CN | 101430279 A | 5/2009 | |
| CN | 103060296 A | 4/2013 | |
| DE | 2730481 A1 | 1/1978 | |
| DE | 19907764 A1 | 11/1999 | |
| EA | 201290985 A1 | 5/2013 | |
| EP | 8780 A2 | 3/1980 | |
| EP | 3035780 A1 | 9/1981 | |
| EP | 0115023 A2 | 8/1984 | |
| EP | 0256127 A1 | 2/1988 | |
| EP | 0283442 A1 | 9/1988 | |
| EP | 304332 A2 | 2/1989 | |
| EP | 0576938 A1 | 1/1994 | |
| EP | 0879772 A2 | 11/1998 | |
| EP | 1010423 A2 | 6/2000 | |
| EP | 1279402 A1 | 1/2003 | |
| EP | 1335706 B1 | 4/2005 | |
| EP | 1579771 A1 | 9/2005 | |
| EP | 1931316 A2 | 6/2008 | |
| EP | 1967211 A1 | 9/2008 | |
| EP | 2079445 A2 | 7/2009 | |
| EP | 2477645 A4 | 7/2012 | |
| EP | 2621476 A1 | 8/2013 | |
| EP | 2621476 B1 | 7/2014 | |
| EP | 2754437 A2 | 7/2014 | |
| EP | 2818160 A1 | 12/2014 | |
| EP | 2741766 B1 | 10/2015 | |
| EP | 2987499 A1 | 2/2016 | |
| ES | 489967 A1 | 10/1980 | |
| FR | 2313916 A1 | 1/1977 | |
| GB | 732951 A | 6/1955 | |
| GB | 1509866 A | 5/1978 | |
| GB | 2234973 A | 2/1991 | |
| JP | S5186113 | 7/1976 | |
| JP | S52-3819 A | 1/1977 | |
| JP | 58-085159 | 5/1983 | |
| JP | S6379589 | 5/1988 | |
| JP | H0398580 A | 4/1991 | |
| JP | H05-38731 A | 2/1993 | |
| JP | 538731 | 10/1993 | |
| JP | H05-76928 B2 | 10/1993 | |
| JP | H1077236 A | 3/1998 | |
| JP | 10-295374 A | 11/1998 | |
| JP | H11-514088 A | 11/1999 | |
| JP | H11315043 A | 11/1999 | |
| JP | 2002506527 A | 2/2002 | |
| JP | 2004-513645 A | 5/2004 | |
| JP | 2004524838 A | 8/2004 | |
| JP | 2006198838 A | 8/2006 | |
| JP | 2008516965 A | 5/2008 | |
| JP | 4187085 B2 | 11/2008 | |
| JP | 2010519217 A | 6/2010 | |
| JP | 2011093845 A | 5/2011 | |
| JP | 2013522284 A | 6/2013 | |
| JP | 2013530811 A | 8/2013 | |
| JP | 2013534141 A | 9/2013 | |
| JP | 2013538846 A | 10/2013 | |
| JP | 6043929 B2 | 12/2016 | |
| KR | 100395722 B1 | 11/2003 | |
| KR | 20060127857 A | 12/2006 | |
| KR | 100804096 B1 | 2/2008 | |
| RU | 94017352 A | 7/1996 | |
| RU | 2445952 C2 | 3/2012 | |
| TW | 201210517 A | 3/2012 | |
| WO | 8705505 A1 | 9/1987 | |
| WO | 90/09428 A1 | 8/1990 | |
| WO | 9009440 A1 | 8/1990 | |
| WO | 90/15856 A1 | 12/1990 | |
| WO | 93/07859 A1 | 4/1993 | |
| WO | 93/18753 A1 | 9/1993 | |
| WO | 9325669 A1 | 12/1993 | |
| WO | 9600773 A1 | 1/1996 | |
| WO | 9610995 A1 | 4/1996 | |
| WO | 9746658 A1 | 12/1997 | |
| WO | 98/01544 A1 | 1/1998 | |
| WO | 97/46860 A3 | 2/1998 | |
| WO | 98/58254 A1 | 12/1998 | |
| WO | 01/25412 A1 | 4/2001 | |
| WO | 01/70047 A1 | 9/2001 | |
| WO | 0174980 A2 | 10/2001 | |
| WO | 0240045 A2 | 5/2002 | |
| WO | 02058735 A1 | 8/2002 | |
| WO | 2004074470 A1 | 9/2004 | |
| WO | 2005042012 A1 | 5/2005 | |
| WO | 2005092370 A1 | 10/2005 | |
| WO | 2006044529 A1 | 4/2006 | |
| WO | 2007013752 A1 | 2/2007 | |
| WO | 2007020259 A2 | 2/2007 | |
| WO | 2007020260 A2 | 2/2007 | |
| WO | WO 2007/020260 * | 2/2007 | ............ A61K 9/36 |
| WO | 08/017659 A1 | 2/2008 | |
| WO | 2008017659 A1 | 2/2008 | |
| WO | 2008102264 A2 | 8/2008 | |
| WO | 2009083607 A1 | 7/2009 | |
| WO | 2009109856 A2 | 9/2009 | |
| WO | 2011035079 A1 | 3/2011 | |
| WO | 2011072069 A2 | 6/2011 | |
| WO | 2011114224 A1 | 9/2011 | |

(56) References Cited

FOREIGN PATENT DOCUMENTS

| WO | 2012019186 A1 | 2/2012 |
|---|---|---|
| WO | 2012042372 A1 | 4/2012 |
| WO | 2012052853 A1 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |

OTHER PUBLICATIONS

Masaki Hasegawa, Direct Compression Microcrystalline Cellulose Grade 12 versus Classic Grade 102, Pharmaceutical Technology, pp. 50-60, May 2002.

International Search Report, Written Opinion and International Preliminary Report on Patentability based on International Application No. PCT/IB2008/000770, dated Jun. 3, 2009; 13 Pages.

Krishnamurty et al., "Delayed release pancrelipase for treatment of pancreatic exocrine insufficiency associated with chronic pancreatitis," Therapeutics and Clinical Risk Management, (2009:5) pp. 507-520.

Drugs@FDA Glossary of Terms, printed Nov. 20, 2009; http://www.fda.gov/Drugs/InformationonDrugs/ucm079436.htm; 7 pages.

Guidance for Industry #191, Changes to Approved NADAs—New NADAs vs. Category II Supplemental NADAs, Final Guidance, U.S. Depailmentof Health and Human Services, Food and Drug Administration, Center for Veterinary Medicine, Released Nov. 19, 2009: 25 pages.

Singapore Written Opinion, corresponding to Singapore Patent Application No. 200905385-1, issued by the Austrian Patent Office dated Dec. 16, 2010; 6 pages.

Hageman, "The Role of Moisture in Protein Stability," Drug Development and Industrial Pharmacy, vol. 14, No. 14, (1988); pp. 2047-2070.

Maul and Schmidt, "Influence of different-shaped pigments on bisacodyl release from Eudragit L 30 D," International Journal of Pharmacetuics, vol. 118, No. 1, May 1, 1995; pp. 103-112.

Maul and Schmidt, "Influence of different-shaped pigments and plasticizers on theophylline release from Eudragit RS30D and Aquacoat ECD30 coated pellets," S.T.P. Pharma Sciences, vol. 7, No. 6, pp. 498-506.

Felton and McGinity, "Influence of Insoluble Excipients on Film Coating Systems," Drug Development and Industrial Pharmacy, vol. 28, No. 3; pp. 225-243.

Parker et al., "Effects of Solids-Loading on Moisture Permeability Coefficients of Free Films," Journal of Pharmaceutical Sciences, vol. 63, No. 1 (Jan. 1974); pp. 119-125.

Thoma and Bechtold, "Influence of aqueous coatings on the stability of enteric coated pellets and tablets," European Journal of Pharmaceutics and Biopharmaceutics, vol. 47, (1999), pp. 39-50.

Nordmark pancreatin brochure, Products all over the World, (publication year unknown); 7 pages.

Australian First Examination Report, dated Mar. 23, 2012, corresponding to Australian Patent Application No. 2008218595; 2 pages.

English Translation of Second Chinese Office Action, dated Apr. 12, 2012, corresponding to Chinese Patent Application No. 200880012762.6; 5 pages.

European Communication, dated Jan. 3, 2012, corresponding to European Patent Application No. 08719392.6 7 pages.

European Communication, dated Aug. 1, 2012, corresponding to European Patent Application No. 08719392.6 7 pages.

New Zealand First Examination Report, dated Aug. 26, 2010, corresponding to New Zealand Patent Application No. 579047; 3 pages.

New Zealand Second Examination Report, dated Dec. 15, 2011, corresponding to New Zealand Patent Application No. 579047; 2 pages.

New Zealand First Examination Report, dated Feb. 29, 2012, corresponding to New Zealand Patent Application No. 598477; 1 page.

Singapore Second Written Opinion, dated Nov. 22, 2011, corresponding to Singapore Patent Application No. 200905385-1; 6 pages.

U.S. Office Action, dated Mar. 20, 2012, corresponding to U.S. Appl. No. 12/034,480; 7 pages.

U.S. Office Action, dated Oct. 14, 2011, corresponding to U.S. Appl. No. 12/034,480; 15 pages.

U.S. Office Action, dated Mar. 19, 2012, corresponding to U.S. Appl. No. 12/034,488; 8 pages.

U.S. Office Action, dated Oct. 25, 2011, corresponding to U.S. Appl. No. 12/034,488; 14 pages.

U.S. Office Action, dated Jan. 4, 2012, corresponding to U.S. Appl. No. 12/034,491; 7 pages.

U.S. Office Action, dated Jun. 23, 2011, corresponding to U.S. Appl. No. 12/034,491; 7 pages.

U.S. Office Action, dated Jun. 26, 2012, corresponding to U.S. Appl. No. 13/019,844; 15 pages.

U.S. Office Action, dated May 24, 2012, corresponding to U.S. Appl. No. 13/019,856; 9 pages.

U.S. Office Action, dated May 23, 2012, corresponding to U.S. Appl. No. 13/019,860; 5 pages.

U.S. Office Action, dated Jul. 2, 2012, corresponding to U.S. Appl. No. 12/832,596; 11 pages.

International Search Report and Written Opinion, dated Oct. 22, 2012, corresponding to International Application No. PCT/US2010/049203; 6 pages.

Canadian Office Action, dated May 6, 2014, corresponding to Canadian Application No. 2,677,989, 2 pages.

Colombian Office Action (with no English translation), dated May 26, 2014, corresponding to Colombian Application No. 09.101.677; 4 pages.

Costa Rica Preliminary Technical Report—1st Phase (with English Translation), dated Jun. 12, 2014, corresponding to Costa Rican Application No. 11031; 11 total pages.

European Communication, dated Apr. 8, 2014, corresponding to European Patent Application No. 08719392.6 6 pages.

English Translation of Indian First Examination Report, dated Oct. 17, 2014, corresponding to Indian Application No. 5854/DELNP/2009; 4 pages.

Singapore Search Report, dated Apr. 7, 2014 and Singapore Written Opinion, dated Apr. 28, 2014, corresponding to Singapore Application No. 2012091583; 11 total pages.

Japanese Decision of Rejection and Decision of Dismissal of Amendment (with English Translations), dated Aug. 25, 2014, corresponding to Japanese Application No. 2009-549868; 9 total pages.

Japanese Notice of Reasons for Rejection (with English translation), dated Jan. 19, 2015, corresponding to Japanese Application No. 2013-265143, 7 total pages.

The Decision of the Enlarged Board of Appeal, dated Nov. 22, 2013, 18 pages.

The Minutes of the Oral Proceedings of Nov. 22, 2013, 6 pages.

Communication from the Enlarged Board of Appeal pursuant to Articles 13 and 14(2) RPEBA, corresponding to Case No. R 06/13, dated Sep. 17, 2013; 6 pages.

Letter from Botti & Ferrari regarding a Petition for Review of Decision T0977/09-3.3.02, European Patent No. 1 335 706 in the name of Aptalis Pharma S.r.l., dated May 15, 2013; 12 pages.

Termination of Opposition Proceedings of Patent No. 01994654.0-1456 /1335706 with Revocation of the Patent, dated Mar. 14, 2013; 2 pages.

Decision, dated Nov. 30, 2012, corresponding to Appeal No. T0977/09-3.3.02; 28 pages.

The Minutes of the Oral Proceedings of Nov. 30, 2012, corresponding to Appeal No. T0977/09-3.3.02 18 pages.

International Search Report, International Preliminary Report on Patentability and Written Opinion of the International Searching Authority, corresponding to International Application No. PCT/IB2012/054050, dated Nov. 14, 2012; 11 total pages.

(56) References Cited

OTHER PUBLICATIONS

A. Aloulou, et al., "In Vitro Comparative Study of Three Pancreatic Enzyme Preparations: Dissolution Profiles, Active Enzyme Release and Acid Stability," Alimentary Pharmacology & Therapeutics, vol. 27, No. 3; Oct. 29, 2007 pp. 283-292.
Final Office Action issued by the U.S. Patent and Trademark Office dated Jul. 14, 2008, corresponding to U.S. Appl. No. 10/416,702, 12 pages.
Mesh to Micron Conversion Chart—Fluideng.com, Copyright 2002—Property of TM Industrial Supply, Inc.; (D20); http://www.fluideng.com/FE/meshmicron.html; 1 page.
English Translation of Example 3 of Priority Document It M12000A002455, Preparation of Pancreatin Pellets Through Direct Spheronisation in Fluid Bed (D21); 1 page.
Summary of facts and submissions, Grounds for the Decision (Annex)—opposition, corresponding to Application No. 01 994 654.0, dated Feb. 23, 2009; 9 pages.
Interlocutory Decision in Opposition proceedings, corresponding to Application No. 01 994 654.0-2107, dated Feb. 23, 2009; 2 pages.
Non-patent literature cited during the Appeal Procedure, related to EP 1 335 706 B1 (Druckexemplar); 8 pages.
Provision of a copy of the minutes in accordance with Rule 124(4) EPC, dated Feb. 23, 2009, corresponding to Application No. 01 994 654.0-2107; 12 pages.
Non-patent literature, dated Jul. 30, 2012, relating to the Appeal Procedure, (Eisenfuhr Speiser); 7 pages.
Letter from Botti & Ferrari, dated Jun. 27, 2012, relating to the Appeal Procedure, 10 pages.
Non-patent literature cited during the Appeal Procedure, (Eisenfuhr Speiser), Grounds of Appeal, dated Jun. 30, 2009; 24 pages.
Letter from Botti & Ferrari, dated Sep. 18, 2009, relating to the Appeal Procedure, 15 pages.
Main Request, Claims with revisions, relating to Appeal Procedure; 1 page.
Description, relating to EP 1 335 706, relating to the Appeal Procedure; 1 page.
Main Request, Claims 1-7, relating to Appeal Procedure; 2 pages.
Royce, et al., Alternative Granulation Technique: Melt Granulation, Drug Development and Industrial Pharmacy, (D4) 22(9&10), 917-924; Copyright 1996 by Marcel Dakker, Inc.
Lombroso, "About the Destruction of the Pancreatic Enzymes by Means of Heat and the Substances that Hamper Such Action", Archivio di Farmacologia Sperimentale e Scienze Affini, Laboratory of Physiology of the R. University of Rome; 14 pages.
Novozyme—Savinase, novozymes, Rethink Tomorrow, Annex 1, A Hard-working, robust protease used to remove protein-based stains; 1 page.
Notice of Opposition to a European Patent and opposition documents related to Patent No. EP 1 335 706 B1, (Opposition file history as of Jan. 14, 2009, excluding non-duplicative, non-administrative documents; (92 total pages).
Non-patent literature dated Sep. 30, 2011, relating to the Appeal Procedure, (Eisenfuhr Speiser); 2 pages.
Non-patent literature cited during the Appeal Procedure, (universitatbonn) (D23), dated Sep. 20, 2011; 15 pages.
Non-patent literature cited during the Apeal Procedure, (One Step Ahead, Granulation and drying for all types of products), Rotolab, (D24); 8 pages.
Sincero, et al., "Detection of hepatitis A virus (HAV) in oysters (Crassostrea gigas)," Water Research, Elsevier, Amsterdam, NL, vol. 40, No. 5, Mar. 1, 2006; pp. 895-902.
Langeveld, et al., "Inactivated recombinant plant virus protects dogs from a lethal challenge with canine parvovirus," Vaccine, Elsevier, vol. 19, No. 27, Jun. 14, 2001, pp. 3661-3670.
Singh, et al., "Canine parvovirus-like particles, a novel nanomaterial for tumor targeting," Journal of Nanobiotechnology 2006, vol. 4, No. 2, dated Feb. 13, 2006; 11 pages.
Shieh, et al., "A method to detect low levels of enteric virus in contaminated oysters", Applied and environmental Microbiology, vol. 65, No. 11, Nov. 1999; pp. 4709-4714.
Bergeron, et al., Genomic Organization and Mapping of Transcription and Translation Products of the NADL-2 Strain of Porcine Parvovirus, Virology, 1993, 197(1): pp. 86-98.
Bergeron, J., Hebert, B. and Tijssen, P., Genomic Organization of the Kresse Strain of Porcine Parvovirus: Identification of the Allotropic Determinant and Comprison with Those of NADL-2 and Field Isolates, Journal of Virology vol. 70, No. 4, Apr. 1996; pp. 2508-2515.
Simpson, et al., "The Structure of Porcine Parvovirus: Comparison With Related Viruses," J. Mol. Biol., 2002, 315(5); pp. 1189-1198.
Szelei, et al., "Porcine Parvovirus". In: Kerr, et al., eds, Parvoviruses, London: Hodder Arnold; 2006; pp. 434-445.
Canaan, et al., "Interfacial Enzymology of Parvovirus Phospholipases A2," Journal of Biologizal Chemistry vol. 279, No. 15, Apr. 9, 2004; p. 14502-14508.
Zadori, et al., 2001, "A Viral Phospholipase A2 is Required for Parvovirus Infectivity," Developmental Cell, vol. 1, Aug. 2001; pp. 291-302.
Zadori, et al., "SAT: a Late NS Protein of Porcine Parvovirus," Journal of Virology, vol. 79, No. 20; Oct. 2005; pp. 13129-13138.
Mullendore, et al., Improved Method for the Recovery of Hepatitis A virus from oysters, Journal of Virological Methods 94, pp. 25-35 (2001).
Sair, et al., "Improved Detection of Human Enteric Viruses in Foods by RT-PCR", Journal of Virological Methods 100, pp. 57-69 (2002).
Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).
Termination of Opposition Proceedings of Patent No. 01994654.0-1456 /1335706 with Revocation of the Patent, dated May 14, 2014; 2 pages.
International Search Report, dated Jun. 23, 2014, corresponding to International Application No. PCT/IB2014/059722 4 pages.
Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.
Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.
U.S. Appl. No. 14/209,365, filed Mar. 13, 2014, cited herewith as U.S. Patent Publication 2014/0276632.
U.S. Appl. No. 14/296,832, Jun. 5, 2014, cited herewith as U.S Patent Publication 2014/0287035.
U.S. Appl. No. 14/237,180, filed Jun. 12, 2014, cited herewith as U.S. Patent Publication No. 2014/0295474.
U.S. Appl. No. 12/400,145, filed Mar. 9, 2009, cited herewith as U.S. Patent Publication No. 2009/0226414.
U.S. Appl. No. 10/416,702, filed May 14, 2003, cited herewith as U.S. Patent Publication 2004/0101562.
U.S. Appl. No. 12/163,530, filed Jun. 27, 2008, cited herewith as U.S. Patent Publication No. 2009/0117180.
U.S. Appl. No. 14/043,923, filed Oct. 2, 2013, cited herewith as U.S. Patent Publication No. 2014/0170212.
U.S. Appl. No. 12/034,480, filed Feb. 20, 2008, cited herewith as U.S. Pat. No. 8,246,950.
U.S. Appl. No. 12/034,488, filed Feb. 20, 2008, cited herewith as U.S. Pat. No. 8,221,747.
U.S. Appl. No. 12/034,491, filed Feb. 20, 2008, cited herewith as U.S. Pat. No. 8,293,229.
U.S. Appl. No. 12/832,596, filed Jul. 8, 2010, cited herewith as U.S. Pat. No. 8,562,978.
U.S. Appl. No. 13/019,844, filed Feb. 2, 2011, cited herewith as U.S. Pat. No. 8,562,979.
U.S. Appl. No. 13/019,856, filed Feb. 2, 2011, cited herewith as U.S. Pat. No. 8,562,980.
U.S. Appl. No. 13/019,860, filed Feb. 2, 2011, cited herewith as U.S. Pat. No. 8,562,981.
U.S. Appl. No. 12/576,930, filed Oct. 9, 2009, cited herewith as U.S. Pat. No. 7,658,918; and.
U.S. Appl. No. 12/568,064, filed Sep. 28, 2009, cited herewith as U.S. Pat. No. 8,784,884.

(56) References Cited

OTHER PUBLICATIONS

International Application No. PCT/IB14/59722, filed Mar. 13, 2014, cited herewith as International Publication No. WO 2014/141121;.
International Application No. PCT/IB14/02583, filed Jul. 15, 2014, cited herewith as International Publication No. WO 2015/019198; and.
International Application No. PCT/IB14/49569, filed Aug. 4, 2014, cited herewith as International Publication No. WO 2015/020943.
A. C. Mehta, "Review of analytical methods used in the dissolution testing of pharmaceuticals", Analytical Proceedings Including Analytical Communications, vol. 31, No. 8, Jan. 1, 1994; pp. 245-248.
Alexey Khrenov: "USP Pancrelipase Update," dated Jul. 1, 2009, and Alexey Khrenov: "USP Enzyme Workshop Pancrelipase Update," dated Jul. 1, 2009; 12 total pages.
"Dissolution Toolkit—Procedures for Mechanical Calibration and Performance Verification Test," USP (U.S, Pharmacopeia), dated Mar. 22, 2010; 16 pages.
New Zealand First Examination Report, dated Oct. 16, 2014, corresponding to New Zealand Application No. 620329; 2 pages.
Colombian Office Action (with English Translation), dated Oct. 29, 2014, corresponding to Colombian Application No. 14-33910; 20 total pages.
Coutlee, et al., "Comparison of Colorimetric, Fluorescent, and Enzymatic Amplification Substrate Systems in an Enzyme Immunoassay for Detection of DNA-RNA Hybrids," Journal of Clinical Microbiology, vol. 27, No. 5, May 1989 pp. 1002-1007.
Fuhrmann, et al., "In Vivo Fluorescence Imaging of Exogenous Enzyme Activity in the Gastrointestinal Tract," Proceedings of the National Academy of Sciences of the USA, vol. 108, No. 22, May 2011; pp. 9032-9037.
Zhang, et al., "Quantitative Fluorescence Correlation Spectroscopy Reveals a 1000-Fold Increase in Lifetime of Protein Functionality," Biophysical Journal, vol. 95, Oct. 2008; pp. 3439-3446.
(Guidance for Industry) "SUPAC-MR: Modified Release Solid Oral Dosage Forms—Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997; 52 pages.
Australian Patent Examination Report No. 1, dated May 20, 2014, corresponding to Australian Application No. 2012293325; 3 pages.
Colombian Office Action (English Summary), corresponding to Colombian Application No. 13-66300; 2 pages.
Eurasian Office Action (with English Translation), dated Jun. 30, 2014, corresponding to Eurasian Application No. 201390409; 5 total pages.
Handbook of Pharmaceutical Excipients, Fifth Edition, Edited by Raymond C. Rowe, et al. 4 pages.
Australian Patent Examination Report No. 1, dated Oct. 14, 2014, corresponding to Australian Application No. 2011309763; 3 pages.
European Search Report, dated Nov. 28, 2014, corresponding to European Application No. 14176579.2; 4 pages.
English translation of Colombian Office Action, corresponding to Colombian Application No. 13-066300; 7 pages.
Masaki Hasegawa, Direct Compression "Microcrystalline Cellulose Grade 12 versus Classic Grade 102," Pharmaceutical Technology, May 2002; pp. 50-60.
Australian Patent Examination Report No. 1, dated Apr. 28, 2014, corresponding to Australian Application No. 2010295494; 3 pages.
Extended European Search Report, dated May 26, 2014, corresponding to European Application No. 10817867.4; 6 pages.
Symersky T., et al. "An Explorative Study on the Effect of Enzymer Supplementation in Patients Recovered From Acute Pancreatitis," Gastroenterology 2004; 126 (4 sippl 2): A85, Abstract 653.
Russian Office Action (with English Translation), dated Jul. 7, 2014, corresponding to Russian Application No. 2012113253; 8 total pages.
Japanese Notice of Rejection (with English Summary Translation), dated Sep. 24, 2014, corresponding to Japanese Application No. 2012-529909; 6 pages.

Russian Office Action (with English translation), dated Nov. 25, 2014, corresponding to Russian Application No. 2012113253; 11 total pages.
Taiwanese Office Action (with English translation), dated Nov. 26, 2014, corresponding to Taiwanese Application No. 099131496; 10 total pages.
Pakistan Examination Report, corresponding to Pakistan Application No. 804/2010; 1 page.
English translation of Israeli Office Action, dated Nov. 23, 2014, corresponding to Israeli Application No. 218656; 2 pages.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-2009-7019590; 6 total pages.
Non-patent literature cited during the Appeal Procedure (universitatbonn) (D22), dated Jun. 17, 2010; 6 pages.
Non-patent literature relating to the Appeal Procedure, dated Aug. 5, 2010, (Eisenfuhr Speiser); 10 pages.
Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Kahn, et al., Bovine Pancreatic Lipase1. II Stability and Effect of Activators and Inhibitors, Journal of Dairy Science, vol. 59, No. 5, pp. 840-846.
Worthington Biochemical Corporation, Lipase—Worthington Enzyme Manual, Triacylglycerol acylhydrolase, (D14) www.worthington-biochem.com; 2 pages.
Caelo, Macrogol 4000 Pulver, Sicherheitsdatenblatt, Seite1, von 3, (D15), dated Aug. 4, 2008; 3 pages.
Answers.com, Stir: Definition, Synonyms of the word "Stir" from Answers.com, (D16), 9 pages.
Office Action issued by the U.S. Patent and Trademark Office dated Apr. 1, 2009, corresponding to U.S. Appl. No. 10/416,702, 24 pages.
US Pharmacopeia, Chapter 786, Particle Size Distribution Estimation by Analytical Sieving, Web download, Jun. 26, 2009; 5 pages.
Gohel, "A Review of Co-Processed Directly Compressible Excipients," J. Pharm. Pharmaceutical Sciences, 8(1); pp. 76-93; (2005).
Priority Document, Italian Patent No. MI2000 A 002456, 25 pages.
Non-patent literature cited during the Appeal Procedure, Eisenfuhr Speiser, Feature Analysis, dated Aug. 5, 2010; 1 page.
International Search Report and Written Opinion of the International Searching Authority, dated Mar. 2, 2015, corresponding to International Application No. PCT/IB2014/002583; 13 total pages.
Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.
International Search Report, and Written Opinion of the International Searching Authority, corresponding to International Application No. PCT/US14/49569, dated Nov. 14, 2014; 8 total pages.
Queensland Government, "Tube Feeding At Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009,15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
Eurasian Office Action dated Jun. 30, 2014 (with English translation), corresponding to Eurasian Application No. 201390409; 5 total pages.
Rowe, et al., Handbook of Pharmaceutical Excipients, 4 pages.
European Search Report corresponding to European Application No. 14176579.2, dated Nov. 28, 2014, 4 pages.
Australian Patent Examination Report No. 2, dated Feb. 25, 2016, corresponding to Australian Application No. 2014203364; 5 pages.

(56) References Cited

OTHER PUBLICATIONS

International Written Opinion of the International Searching Authority and International Search Report dated Jan. 19, 2010, corresponding to International Application No. PCT/IB2009/000472; 7 total pages.
International Preliminary Report on Patentability and Written Opinion of the International Searching Authority, dated Jan. 26, 2016, corresponding to International Application No. PCT/IB2014/002583; 10 total pages.
European Search Report dated Jan. 22, 2016, corresponding to European Application No. 15178147.3; 9 pages.
Communication of the Board of Appeal, corresponding to Appeal No. T2255/12-3.3.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Botti & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patent No. 1 931 316, dated May 2, 2012; 1 page.
Non-Patent Literature document—"Submission in opposition proceedings," issued by the European Patent Office, corresponding to European Patent No. 1 931 316, dated May 2, 2012; 1 page.
Non-Patent Literature document—"Reply to summons to attend oral proceedings; filing of new main claim Yequest," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.
Non-Patent Literature document—Letter from Europatent to European Patent Office, corresponding to European Patent No. 1 931 316, dated Feb. 6, 2012; 1 page.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1 (2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Non-Patent Literature document—"Notice of Opposition against the European Patent EP-B-1 931 316", (letter from Botti & Ferrari to the European Patent Office), dated Nov. 15, 2010, 12 pages.

Non-Patent Literature Document—"Aqueous Coating—Aquacoat ECD," FMC Biopolymer; 12 pages.
Non-Patent Literature document—"Brief Communication," dated Feb. 10, 2011, issued by the European Patent Office, corresponding to European Application No. 06778240.9 (European Patent No. 1 931 316); 1 page.
Non-Patent Literature document—"Vollmacht Authorisation Pouvoir," (German document—Power of Representation before the EPO for European Patent No. 1 931 316, dated Sep. 13, 2011; 3 total pages.
Non-Patent Literature document—"Claims—First Auxiliary Request" and "Claims—Second Auxiliary Request," dated Sep. 2011, corresponding to Opposition Proceedings of European Patent No. 1 931 316; 12 total pages.
Non-Patent Literature document—"Brief Communication—Main Request,", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to Euoprean Patent No. 1 931 316, dated Jan. 21, 2010; 2 pages.
Non-Patent Literature document—"A2PAMPHLET," related to WO 2007/020259 (PCT/EP2006/065311), printed on May 19, 2008; 29 total pages.
Non-Patent Literature document—"Claims (EP 06 778 240)," printed Sep. 25, 2008; 12 total pages.
Naftifine HCI—MSDS—Material Safety Data Sheet, created Jun. 23, 2004; http://pharmacycode.com/msds/Maftifine_HCI; 4 pages.
Japanese Office Action (with English translation), dated Mar. 1, 2016, corresponding to Japanese Application No. 2014-524476; 5 total pages.
International Preliminary Report on Patentability and Written Opinion of the International Searching Authority, dated Feb. 9, 2016, corresponding to International Application No. PCT/US2014/049569; 7 total pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Colombian Office Action (No English translation available), dated Feb. 19, 2016, corresponding to Colombian Application No. 14 026.502; 8 pages.
Malaysian Office Action dated Mar. 31, 2016, corresponding to Malaysian Application No. PI 2012001215; 3 pages.
Sankalia M.G et al., "Papain Entrapment in Alginate Beads for Stability Improvement and Site-Specific Delivery Physicochemical Characterization and Factorial Optimization Using Neural Network Modeling," AAPS PharmSciTech., 2005; vol. 6, No. 2, Article 31; pp. E209-E222.
Scheich C et al., "An Automated In Vitro Protein Folding Screen Applied to a Human Dynactin Subunit," Protein Science, 2004, vol. 13; pp. 370-380.
Miller DA et al., "Evaluation of the USP Dissolution Test Method a for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; p. 12488-12496.
Eurasian Office Action (with English translation), dated May 30, 2016, corresponding to Eurasian Application No. 201590835/28; 4 total pages.
Eurasian Office Action (with English translation), dated May 30, 2016, corresponding to Eurasian Application No. 201590836/28; 4 total pages.
Eurasian Office Action (with English translation), dated Jun. 8, 2016, corresponding to Eurasian Application No. 201390409/28; 4 total pages.
English translation of Israeli Office Action dated Jan. 11, 2016, corresponding to Israeli Patent Application No. 225504; 3 pages.

(56) References Cited

OTHER PUBLICATIONS

English translation of Chinese Second Office Action dated Dec. 21, 2015, corresponding to Chinese Application No. 201410059861.7; 5 pages.
Taiwanese Office Action (with English translation), dated Nov. 3, 2015, corresponding to Taiwanese Application No. 102138934; 16 total pages.
Japanese Office Action (with English translation), dated May 12, 2015, corresponding to Japanese Patent Application No. 2013-530811; 8 total pages.
International Search Report and Written Opinion of the International Searching Authority dated Nov. 20, 2015, corresponding to International Application No. PCT/IB2015/001237; 17 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
Russian Office Action (with English translation), dated Oct. 29, 2015, corresponding to Russian Application No. 2014104591; 7 total pages.
Mesh to Micron Conversion Chart—Fluideng.com, Copyright 2002—Property of TM Industrial Supply, Inc.; (D20); http://www.fluideng.com/FE/meshmicron.html; Jun. 30, 2009; 1 page.
European Examination Report dated Dec. 4, 2018, corresponding to European Application No. 14 859 866.7; 5 pages.
Singapore Search Report and Examination Report dated Feb. 9, 2018, corresponding to Singapore Application No. 10201405791X; 6 total pages.
Dominguez-Munoz et al., "Effect of Oral Pancreatic Enzyme Administration on Digestive Function in Healthy Subjects: Comparison Between Two Enzyme Preparations," Aliment Pharmacol Ther. 11, vol. 13, No. 2, Apr. 1, 1997; pp. 403-408.
Japanese Office Action dated Dec. 12, 2017, corresponding to Japanese Application No. 2016-196831; 3 total pages.
Chinese Office Action dated Jun. 2, 2017,. corresponding to Chinese Application No. 201480027549.8; 7 pages.
Russian Office Action and Search Report (with English translation) dated Feb. 16, 2018, corresponding to Russian Application No. 2016103606; 13 total pages.
Russian Decision to Grant (with English translation), dated Feb. 27, 2018, corresponding to Russian Application No. 2015138541/15; 12 total pages.
Russian Office Action and Search Report (with English translation), dated Nov. 9, 2017, corresponding to Russian Application No. 2015138541/15; 17 total pages.
Australian Examination Report dated Jan. 8, 2018, corresponding to Australian Application No. 2014229330; 4 pages.
English translation of Japanese Office Action dated Feb. 27, 2018, corresponding to Japanese Application No. 2016-528615; 13 pages.
Korean Notice of Allowance (with English translation), dated Dec. 6, 2017, corresponding to Korean Application No. 10-2015-7004820; 3 pages.
Australian Examination Report dated Oct. 11, 2017, corresponding to Australian Application No. 2016204414; 3 pages.
Singapore Notice of Eligibility for Grant, including Examination Report and Search Report, dated Feb. 27, 2018, corresponding to Singapore Application No. 10201405791X; 9 total pages.
Russian Office Action and Search Report (with English translation) dated Nov. 9, 2017, corresponding to Russian Application No. 2015138541; 11 total pegs.
English Translation of Japanese Office Action dated Nov. 6, 2017, corresponding to Japanese Application No. 2015-562502; 5 pages.
Japanese Office Action (wish English translation), dated Nov. 14, 2017, corresponding to Japanese Application No. 2015-562502; 10 total pages.
English translation of Russian Office Action and Search Report dated Feb. 16, 2018, corresponding to Russian Application No. 2016103606; 6 total pages.
Japanese Office Action (with English translation) dated Mar. 27, 2018, corresponding to Japanese Application No. 2016-53356; 10 total pages.

Eiyogaku Zasshi (Nahomi Imaeda) "Food Composition Table for Retort-Packaged Baby Foods", Department of Food Science and Nutrition, Faculty of Human Life and Environmental Sciences, Nagoya Women's University, Jpn. J. Nutr. Diet, 2008, vol. 66, No. 5; pp. 255-262.
Ensure Plus milkshake style, 2015 (online), [search Mar. 13, 2018], Retrieved from the internet, URL: http://www.abbottnutrition ie/content/datasheets/Ensure_Plus_datasheet_January_2015.pdf.
European Communication dated Mar. 5, 2018, corresponding to counterpart European Application No. 15 750 805.2 5 pages.
Solvay Pharmaceuticals: "Solvay Pharmaceuticals Creon (Pancrelipase Delayed-Release Capsules) Antiviral Drugs Advisory Committee, Dec. 2, 2008, Open Session (Appendices 1 and 2 for Closed Session under separate cover) Available for Public Disclosure Without Redaction"; Dec. 2, 2008 (XP055454900); Retrieved from the Internet: https://www.fda.gov/ohrms/dockets/ac/08/briefing/2008-4402b1-03-SOLVAY.pdf; 137 pages.
Canadian Office Action and Examination Search Report, dated Apr. 27, 2018 corresponding to counterpart Canadian Application No. 2,843,556; 6 total pages.
European Communication dated Dec. 4, 2017, corresponding to European Application No. 14859866.7; 5 pages.
English translation of Korean Office Action dated Mar. 29, 2018, corresponding to Korean Application No. 10-2013-7010970; 3 pages.
Notice of Opposition to a European Patent, European Patent No. EP2621476, dated Apr. 29, 2018 and related opposition documents; 1059 total pages.
Ndian Examiantion Report dated Dec. 19, 2017, corresponding to Indian Application No. 3078/CHENP/2013; 5 pages.
Taiwanese Office Action with English tranlsation of Search Report, dated May 13, 2016, corresponding to Taiwaense Application No. 099131496; 5 total pages.
Australian Patent Examination Report No. 3, dated Jun. 28, 2016, corresponding to Australian Application No. 2014203364; 3 pages.
English translation of Chinese Third Office Action, dated Jun. 28, 2016, corresponding to Chinese Application No. 201410059861.7; 4 pages.
Korean Office Action (with English translation) dated May 16, 2016, corresponding to Korean Application No. 10-2015-7004820; 10 total pages.
English translation of Israeli Office Action, dated Sep. 29, 2016, corresponding to Israeli Application No. 241540; 2 pages.
European Communication dated Jan. 2, 2017, corresponding to European Application No. 14 717 867.7; 5 pages.
English translation of Israeli Office Action dated Aug. 30, 2016, corresponding to Israeli Application No. 243627; 2 pages.
Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.
Tolin et al., "Purification and Serology of Peanut Mottle Virus", The American Phytopathological Society, vol. 73, No. 6, 1983; pp. 899-903.
Casas et al., "Detection of enterovirus and hepatitis A virus RNA in mussels (Mytilus spp.) by reverse transcriptase-polymerase chain reaction", Journal of Applied Microbiology, vol. 90, 2001; pp. 89-95.
Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 8, Aug. 1988; pp. 1983-1988.
Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.
European Communication and Supplemental Partial European Search Report, dated Nov. 14, 2016, corresponding to European Application No. 14859866.7, 9 pages.
European Communication dated Sep. 29, 2016, corresponding to European Application No. 10 817 867.4; 3 pages.

(56) References Cited

OTHER PUBLICATIONS

Korean Office Action (with English translation), dated Nov. 11, 2016, corresponding to Korean Application No. 10-2012-7009516; 12 total pages.
Israeli Office Action dated Jan. 16, 2017, corresponding to Israeli Application No. 218656; 2 pages.
Israeli Office Action dated Jan. 17, 2017, corresponding to Israeli Application No. 245875; 2 pages.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, (1997); pp. 498-506.
Handbook of Pharmaceutical Excipients, Fifth Edition, Edited by Raymond C. Rowe, et al. (Aug. 2005) 4 pages.
Kahn, et al., Bovine Pancreatic Lipase1 II. Stability and Effect of Activators and Inhibitors, Journal of Dairy Science, vol. 59, No. 5, Apr. 1975; pp. 840-846.
Description, relating to EP 1 335 706, paragraphs [0022] through [0036], relating to the Appeal Procedure (E8); 1 page.
Novozymes—Savinase, novozymes, Rethink Tomorrow, Annex 1, A Hard-working, robust protease used to remove protein-based stains; Copyright 2008 Novozymes; 1 page.
Non-patent literature cited during the Appeal Procedure, (One Step Ahead, Granulation and drying for all types of products), Rotolab, (D24); Jun. 28, 2012; 8 pages.
Arbocel Product Sheet, J. Rettenmaier & Bohne Gmbh & Co. (JRS); 1 page.
Alexey Khrenov, "USP Enzyme Workshop: Pancrelipase update", (Jul. 1, 2009), URL:http://www.usp.org/meetings-courses/workshops/past-usp-workshops/usp-enzyme-workshop, (Nov. 6, 2012), XP055043191 [A] 1-26 the whole document (Document Not Available).
Wikipedia Search Result for Mehl (Flour in English) (English translation also attached); printed from www.wikipedia.com on Feb. 2, 2017; 18 total pages.
European Communication dated Mar. 2, 2017, corresponding to European Application No. 15 178 147.3; 6 pages.
European Extended Search Report dated Feb. 15, 2017, corresponding to European Application No. 14833670.4; 9 pages.
"Ensure Plus HN", IP.com Journal, IP.COM Inc., West Henrietta, NY, US, Feb. 9, 2002 (This document completes the disclosure of US2012/177629 with respect to the composition of the product Ensure Plus); 1 page.
Sackman et al., "Does Mixing Pancreatic Enzyme Microspheres (Pancrease) with Food Damage the Enteric Coating?", Journal of Pediatric Gastroenterology and Nutrition, Jan. 1, 1982; pp. 333-335.
Shlieout et al., "Administration of CREON Pancrelipase Pellets via Gastrostomy Tube is Feasible with no Loss of Gastrict Resistance or Lipase Activity—An In Vitro Study", Clinical Drug Investigation, vol. 31, No. 7, Jan. 1, 2011 pages e1-e7.
English translation of a UAE Search Report and Examination Report issued by the UAE Patent Office dated Oct. 31, 2016, corresponding to UAE Application No. 743/2009; 15 total pages.
Canadian Office Action and Examination Search Report, dated Nov. 18, 2016, corresponding to Canadian Application No. 2,677,989; 3 total pages.
English translation of CHinese Office Action dated Jan. 20, 2017, corresponding to Chinese Application No. 201410059861.7; 4 total pages.
Australian Examination Report No. 1, dated Feb. 8, 2017, corresponding to Australian Application No. 2016204414; 5 pages.
Nakamura et al., "Effects of High-Lipase Pancreatin on Fecal Fat, Neutral Sterol, Bile Acid, and Short-Chain Fatty Acid Excretion in Patients with Pancreatic Insufficiency Resulting from Chronic Pancreatitis," International Journal of Pancreatology, Feb. 1998; vol. 23, No. 1; pp. 63-70.
G. J. Peschke, "Active Components and Galenic Aspects of Enzyme Preparations," Pancreatic Enzymes in Health and Disease, Springer-Verlag Berlin Heidelberg, 1991; pp. 55-64.

Canadian Office Action and Examination Search Report, dated Aug. 16, 2017, corresponding to Canadian Application No. 2,812,862; 4 total pages.
Korean Office Action (with English Translation) dated Sep. 5, 2017, corresponding to Korean Application No. 10-2013-7010970; 12 total pages.
Russian Search Report (with English translation) dated Sep. 10, 2018, corresponding to Russian Application No. 2015155470/15; 4 total pages.
Japanese Office Action (English translation) dated Aug. 28, 2018, corresponding to Japanese Application No. 2016-552457; 12 pages.
European Communication dated Sep. 13, 2018, corresponding to European Application No. 14 859 866.7; 6 pages.
Chinese third Office Action dated Aug. 20, 2018, corresponding to Chinese Application No. 2014800275498; 6 pages.
European Communication dated Jul. 19, 2018 and issued in corresponding European Patent Application No. 14833670 4, 6 pages.
Otilia May Yue Koo, et al., "The Influence of Microcrystalline Cellulose Grade on Shape and Shape Distributions of Pellets Produced by Extrusion-Spheronization," Chem. Pharm. Bull., Nov. 2001, vol. 49, No. 11, pp. 1383-1387.
Citation cited in Notice of Oppoisition dated Nov. 8, 2017, corresponding to European Application No. EP14176579 2, Mannitol, pp. 424-428.
Citation cited in Notice of Oppoisition dated Nov. 8, 2017, corresponding to European Application No. EP14176579.2, Fmc BioPolymer, the Science of Fomulation, Product information brochure for Avicel PH, (21 total pages).
Armstrong et al., Handbook of Pharmaceutical Excipients, Sixh Edition, Feb. 5, 2009, Edited by Raymond C. Rowe, et al., Cellulose, Microcrystalline; pp. 129-133.
Citation cited in Notice of Oppoisition dated Nov. 8, 2017 corresponding to European Application No. 14176579.2); Product Information leaflet (59755) for Arbocel BC200, Kremer Pigmente; 1 page.
Citation cited in Notice of Oppoisition dated Nov. 8, 2017 corresponding to European Application No. 14176579.2); Product Information leaflet for EXPLOTAB—Sodium Starch Glycolate from JRS Pharma—Product Desciption and Details, American Pharmaceutical Review, 2 pages.
Notice of Oppoisition to European Patent No. EP2818160 (European Application No. 14176579.2), dated Nov. 8, 2017; 35 total pages.
Van de Vijver, et al., Treatment of Infants and Toddlers With Cystic Fibrosis-related Pancreatic Insufficiency and Fat Malaborption With Pancrelipase MT, Original Article: Gastroenterology, JPGN, Jul. 2011, vol. 53, No. 1, pp. 61-64.
Eurasian Office Action (with English Translation) dated Sep. 6, 2017, corresponding to Eurasian Application No. 201590835/28; 2 total pages.
Eurasian Office Action (with English Translation) dated Sep. 6, 2017, corresponding to Eurasian Application No. 201590836/28; 2 total pages.
Eurasian Office Action (with English translation), dated Dec. 19, 2016, corresponding to Eurasian Application No. 201390409/28; 4 total pages.
Australian Patent Examination Report No. 1, dated Sep. 21, 2016, corresponding to Australian Application No. 2015243026; 3 pages.
Curopean Communication dated Apr. 11, 2017, corresponding to European Application No. 14859866.7; 1 page.
European Search Report dated Mar. 24, 2017, corresponding to European Application No. 14859866.7; 21 total pages.
Australian Examination Report, dated Apr. 10, 2017, corresponding to Australian Application No. 2016216662; 3 pages.
European Communication dated May 19, 2017, corresponding to European Application No. 10817867.4; 3 pages.
European Communication dated Aug. 2, 2017, corresponding to European Application No. 15 178 147.3; 8 pages.
Opekun, Jr. et al., "Lack of dose-response with Pancrease MT for the treatement of exocrine pancreatic insufficiency in adults," Blackwell Science Ltd., Aliment Pharmacol Then (1997), vol. 11; pp. 981-986.
"Clinical Pharmacology and Biopharmaceutics Revew(s)", Center for Drug Evaluation and Research, Apr. 23, 2010, Application No.

(56) References Cited

OTHER PUBLICATIONS

022523Orig1s000; 37 pages—Retrieved from the Internet: https:www.accessdata.fda.gov/drugsatfda_docs/nda/2010/022523orig1s000clinpharmr.pdf.
"Pancrease MT Capsules", Aug. 2005, Drug Reference Encyclopedia; 7 pages—Retrieved from the Internet: https://theodora.com/drugs/pancrease_mt_capsules_mcneil_consumer.html.
European Communication dated Sep. 15, 2017, corresponding to European Application No. 14 815 008.9; 7 total pages.
Argentine Office Action dated Mar. 31, 2017, corresponding to Argentine Application No. P080100693; 6 pages (No English language translation available).
Taiwanese Office Action (with English translation), dated Feb. 16, 2017, corresponding to Taiwanese Aplication No. 102138934; 5 total pages.
Examination Report and Search Report issued by the Korean Intellectual Property Office dated Jul. 3, 2017, corresponding to AE Application No. UAE/P/0743/2009; 13 total pages.
Opposition filed in EP 2621476 dated Aug. 5, 2015, 22 pages.
International Search Report and Written Opinion of the International Searching Authority, corresponding to International Application No. PCT/US14/63984, dated Mar. 13, 2015; 10 total pages.
Chinese First Office Action and Search Report (English translations), dated Apr. 3, 2015, corresponding to Chinese Patent Application No. 201410059861.7; 23 total pages.
Israeli Office Action dated May 10, 2015 (no English translation), corresponding to Israeli Patent Application No. 200407; 2 pages.
European extended Search Report, dated Jun. 2, 2015, corresponding to European Patent Application No. 14150794.7; 10 pages.
Communication of a Notice of Oppoistion to a European Patent Application and opposition documents related to Patent Application No. EP 117885223.3, dated Aug. 5, 2015 (678 total pages).
Arbocel Product Sheet.
Wikipedia Search Result for Mehl (No English translation).
U.S. Appl. No. 61/389,037, filed Oct. 1, 2010 (prosecution history).
Eurasian Office Action (With English Translation) dated Oct. 30, 2015, correpsonding to Eurasian Application No. 201390409128; 4 total pages.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.

International Preliminary Report on Patentability and Written Opinion of the International Searching Authoirty, corresponding to International Application No. PCT/IB2014/059722, dated Sep. 15, 2015; 9 Pages.
Canadian Office Action dated Jul. 3, 2015, corresponding to Canadian Patent Application No. 2,774,269; 4 pages.
English translation of Japanese Notice of Rejection, dated Jul. 7, 2015, corresponding to Japanese Patent Application No. 2012-529909; 2 pages.
Chilean Office Action (No English Translation Available) dated Jul. 22, 2015, corresponding to Chilean Patent Application No. 00658-2012; 8 pages.
Australian Patent Examination Report 1, dated Sep. 15, 2015, corresponding to Australian Patent Application No. 2014253526; 3 pages.
Russian Office Action (with English translation), dated Jun. 15, 2015, corresponding to Russian Patent Appplication No. 2014104591/15; 10 total pages.
Colombian Office Action (No. English Translation Available), dated Sep. 30, 2015, corresponding to Colombian Application No. 14-33910; 11 pages.
European Communication dated Jul. 6, 2015, corresponding to European patent application No. 14150794.7; 2 pages.
Korean Notice of Preliminary Rejection (with English translation), dated Jun. 12, 2015, corresponding to Korean patent application No. 10-2015-7004820; 16 total pages.
Australian Patent Examination Report No. 1, dated Jul. 6, 2015, corresponding to Australian Patent Application No. 2014203364; 4 pages.
Canadian Office Action and Examination Search Report dated Sep. 3, 2015, corresponding to Canadian Patent Application No. 2,677,989; 4 total pages.
Japanese Decision of Rejection (with English translation) dated Sep. 25, 2015, corresponding to Japanese Applcation No. 2013-265143; 9 total pages.
Eurasian Search Report (with English translation) issued by the EUrasian Patent Organization (EAPO) dated Sep. 16, 2015, corresponding to Eurasian Patent Application No. 201590836; 4 total pages.
Eurasian Search Report (with English translation) issued by the EUrasian Patent Organization (Eapo) dated Sep. 16, 2015, corresponding to Eurasian Patent Application No. 201590835; 4 total pages.
Ukrainian Office Action (with English Translation) dated Sep. 23, 2015, corresponding to Ukraine Application No. a 2013 03847; 11 total pages.

* cited by examiner

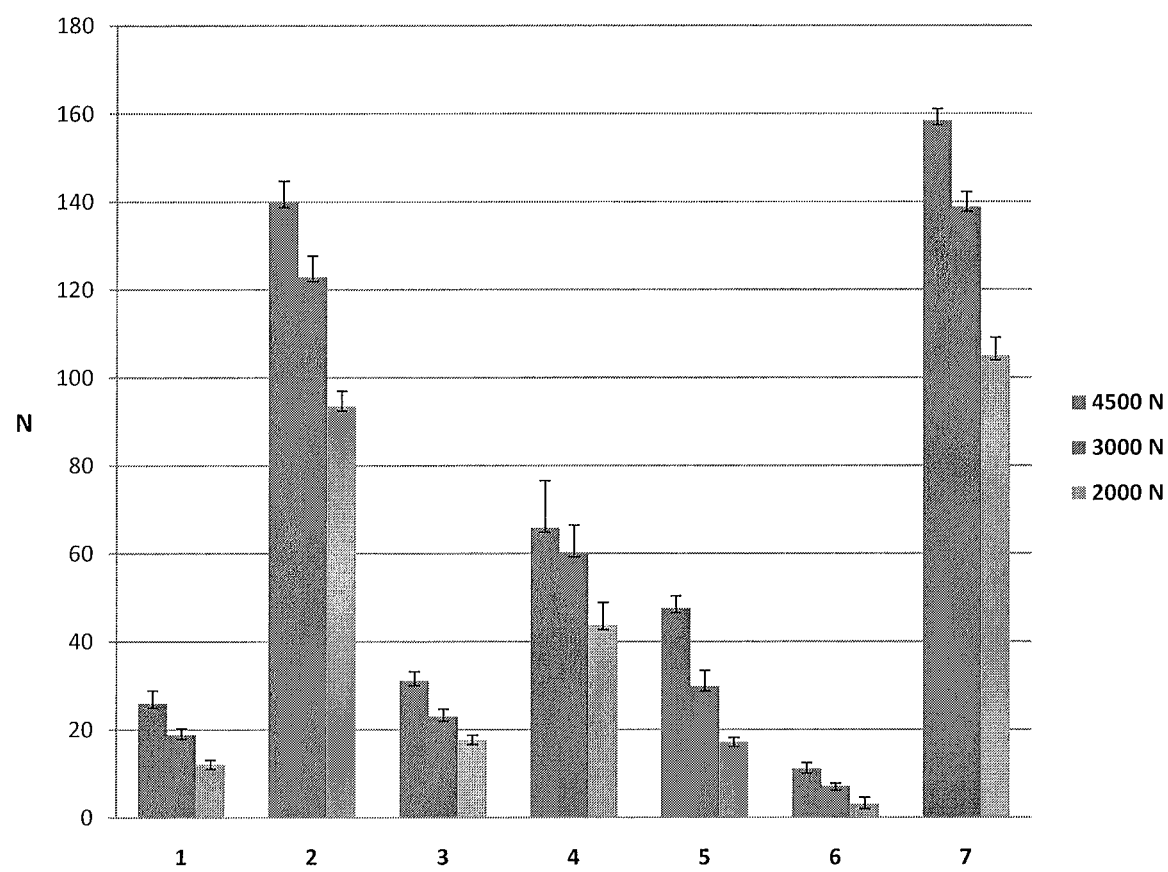

STABLE LOW DIGESTIVE ENZYME CONTENT FORMULATION

CROSS-REFERENCE TO RELATED APPLICATIONS

This application claims priority to U.S. Provisional Application Ser. No. 61/389,037, filed Oct. 1, 2010, which is herein incorporated by reference in its entirety.

FIELD OF THE INVENTION

In various embodiments, the present invention is directed to pharmaceutical compositions having a stable, low (diluted) digestive enzyme content comprising at least one digestive enzyme and at least one carrier, or a dosage form thereof. In other embodiments, the invention is also directed to processes of preparation of the composition or the dosage form. In additional embodiments, the invention is directed to the treatment and prevention of disorders associated with a digestive enzyme deficiency in a patient in need thereof, comprising administering to said patient a pharmaceutically acceptable amount of the composition having a stable low digestive enzyme content or dosage form thereof.

BACKGROUND OF THE INVENTION

The proper dosing of medications for patients is an important concern within the medical field. For infants or smaller children, or geriatric patients in particular, and sometimes also for adult populations, the administration of medications and dosing methods often present substantial issues. As is well known in the art, medications are provided in many forms (e.g., liquid, solid, and combinations of solids in liquids) and are delivered to patients in many ways (e.g., orally, via injection, transdermally).

The FDA estimates that more than 200,000 Americans suffer from exocrine pancreatic insufficiency (EPI). EPI involves a physiological disorder wherein individuals are incapable of properly digesting food due to a lack of digestive enzymes made by their pancreas. That lack of digestive enzymes leads to disorders such as the maldigestion and malabsorption of nutrients, which lead to malnutrition and other consequent undesirable physiological conditions associated therewith. These disorders are common for those suffering from cystic fibrosis (CF) and other conditions compromising the exocrine function of the pancreas, such as pancreatic cancer, pancreatectomy, and pancreatitis. The malnutrition can be life threatening if left untreated, particularly in the case of infants and CF patients, and the disorders can lead to impaired growth, compromised immune response, and shortened life expectancy.

Digestive enzymes, such as pancrelipase and other pancreatic enzymes products (PEPs), can be administered to at least partially remedy EPI. The administered digestive enzymes provide for patients to be able to more effectively digest their food. Enzyme therapy is a critical aspect of clinical management of nutrition and digestion in the CF population. Recently published infant guidelines recommend immediate initiation of PERT (pancreatic Enzyme Replacement Therapy) in CF newborns with symptomatic or confirmed pancreatic insufficiency. Within this framework an optimal dosing regimen has to be identified. It is believed that the use of PERT in infants may improve short and long term growth and nutritional outcomes, and subsequently increase lung function and ultimately survival.

Pancreatic enzymes, which have been used in the treatment of EPI to compensate for lost of digestive function, have been in use for more than 60 years. Their use until recently was not subject modern regulatory guidelines governing drug approvals based on safety, and efficacy, and manufacturing controls. Recently, pancreatic enzyme replacement therapies have become the subject of US and European regulatory authority initiatives that require that marketed pancreatic enzyme products go through the current drug approval process in order to remain in commerce. Zenpep®, Creon® and Pancreaze® are three products that successfully went through the process set by the FDA and are approved for marketing in the United States. In other territories/countries where similar initiatives are still proceeding or have not been implemented as yet, a variety of pancreatic enzyme products are still available.

Capsules containing digestive enzymes such as pancrelipase have been developed for oral administration. However, if a patient is unable to swallow the capsules, each capsule can be opened and the contents sprinkled on a small amount of food, usually a soft, acidic food (such as commercially available applesauce) and administered orally to the patient with a spoon. Alternatively such medications may be administered orally for infants and children, using a syringe device containing the contents suspended in a medium amenable to administration thereby.

The pancrelipase products are generally labeled as containing three enzyme classes: lipase, amylase, and protease, and the levels or potency of which are listed. These enzymes catalyze the hydrolysis of fats into glycerol and fatty acids, starch into dextrin and sugars, and proteins into amino acids and derived substances. Digestion is, however, a complex process involving many other enzymes and substrates that contribute to correct digestive functioning and producing the full range of digestive products. Other enzymes contained in pancrelipase include trypsin, carboxypeptidases, elastases, phospholipases, and cholesterases amongst other and various co-factors and coenzymes. These substances are produced naturally in the pancreas and also contribute to correct digestive functioning.

Pancrelipase is typically prepared from porcine pancreatic glands, although other sources can also be used, for example those described in U.S. Pat. No. 6,051,220, U.S. 2004/0057944, 2001/0046493, and WO 2006044529, each of which is herein incorporated by reference in its entirety for all purposes.

Pancreatic enzymes show optimal activity under near neutral and slightly alkaline conditions. Under gastric conditions, pancreatic enzymes may be inactivated with a resulting loss in biological activity. Therefore, exogenously administered enzymes are generally protected against gastric inactivation and remain intact during their transit through the stomach and into the duodenum. Therefore it is desirable to coat pancreatic enzymes. Pancreatic lipases are the most sensitive to gastric inactivation and are the most important class of enzymes in the treatment of malabsorption. Lipase activity is typically monitored to determine the stability of an enzyme composition containing lipase.

The entire contents of U.S. Pat. No. 7,658,918 issued to Ortenzi et al. is expressly incorporated by reference in its entirety herein for all purposes. U.S. Pat. No. 7,658,918 describes stable digestive enzymes compositions and explains that certain particulate medications, administered orally, are designed to pass through the stomach of the patient and thereafter to release within the intestines; the total amount of pancrelipase (by weight) in the cores of the particles comprised in the compositions or oral dosage forms disclosed in said patent is 68-90%.

Aptalis Pharma markets at least some multiparticulate enterically coated pancrelipase enzymes beads medications. For example, Aptalis Pharma markets delayed-release capsules for the treatment of exocrine pancreatic insufficiency (EPI) in patients under the designation EUR-1008 and the registered trademark Zenpep®. Each Zenpep® capsule for oral administration contains enteric coated beads with high pancrelipase content (1.8-1.9 mm for 3,000, 5,000 USP units of lipase, 2.2-2.5 mm for 10,000, 15,000 and 20,000 and 25,000 USP units of lipase).

All of the marketed pancrelipase products have very high pancrelipase content.

Some commercially available digestive enzyme compositions show a loss of lipase activity over time of up to about 35% or more. In order to compensate for the loss of enzymatic activity during storage and to ensure that the product provides the label-claimed potency at the end of the shelf life, manufacturers typically overfill the dosage forms from 5% to 60% and current USP specifications for Pancrelipase Delayed-Release Capsules allow for Pancrelipase equivalent to not less than 90% and not more than 165% of the labeled lipase activity. In practice this means that patients and prescribers are sometimes unable to judge the dosage strength with accuracy, with the practical result that the appropriate dosage needs to be determined empirically for each new prescription. Patients with exocrine pancreatic insufficiency disorders rely on these drugs to provide the enzymes they need to digest food properly. If the label contains an inaccurate statement about a particular product's potency, then the patient is at risk for receiving too much or too little of the medicine.

In addition, there exist several situations in which a low dosage is needed and proper dosing of the medication cannot be achieved using the existing high dosage formulations. This becomes particularly relevant when pancrelipase should be a administered in infants with a dose ranging from 500 units lipase per meal per kg body weight to 2,000 units lipase per meal per kg then, low dosage or diluted pancrelipase dosage form should be available for administration.

It is generally known that the preparation of low dosage forms having a uniform drug content faces several problems. In addition to that, in case of pancrelipase, both the composition and the process of preparation of a final diluted formulation should be as such as to ensure the proper stability upon storage of the labile enzymes.

Accordingly, it would be desirable to provide a stable low dosage or diluted digestive enzymes composition having high content uniformity and capable of maintaining the necessary activity for the expected shelf life of the enzymes preparation.

BRIEF SUMMARY OF THE INVENTION

To achieve these and other objects, and to meet these and other needs, and in view of its purposes, the present invention relates to a stable low dosage digestive enzyme composition, and dosage form comprised thereof.

More particularly, in various embodiments, the present invention relates to a stable, highly diluted enzyme composition and dosage form that comprise a plurality of digestive enzymes beads, more particularly enterically coated beads. The diluted digestive enzyme beads have high content uniformity and exhibit minimal loss of enzymatic activity upon storage.

The present invention provides for a suitable package comprising a sealed container made of moisture resistant material, a desiccant, and at least one dosage form according to the invention.

Moreover, the present invention provides a method of preparing the stable, low dosage digestive enzyme composition and dosage form thereof. The method comprises preparing a suitable diluted digestive enzyme blend with at least one carrier to ensure the high uniformity in digestive enzyme content, and then coating the beads with a solution comprising an enteric polymer, thereby forming a plurality of stable enterically coated diluted digestive enzyme-containing beads.

BRIEF DESCRIPTION OF THE FIGURE

FIG. 1. Hardness of tablets consisting of pancrelipase and a carrier (blend 1: pancrelipase; blend 2: pancrelipase and microcrystalline cellulose B; blend 3: pancrelipase and trehalose; blend 4: pancrelipase and isomalt; blend 5: pancrelipase and calcium bibasic; blend 6: pancrelipase and inostol; blend 7: pancrelipase and microcrystalline cellulose A).

DETAILED DESCRIPTION OF THE INVENTION

The present invention is directed to a stable composition comprising at least one digestive enzyme, and at least one carrier wherein:
a) the total amount of digestive enzymes in the composition is from about 4 to about 20% by weight; or
b) at least one carrier of the composition has a large particle size; or
c) the total amount of digestive enzymes in the composition is from about 4 to about 20% by weight, and at least one carrier of the composition has a large particle size.

In another embodiment, the total amount of the digestive enzymes in the composition ranges from about 5 to about 19% by weight.

In another embodiment, the total amount of the digestive enzymes in the composition ranges from about 10 to about 15% by weight. In another embodiment of the invention, the total amount of the digestive enzymes in the composition ranges from about 4%, or about 5%, or about 10%, or about 15%, or about 19% by weight, inclusive of all ranges and sub-ranges there between.

In the composition of the invention, the digestive enzymes are in form of beads, preferably in the form of enterically coated pancrelipase beads.

In various embodiments of the invention, the diluted digestive enzymes beads comprise: from about 4 to about 20 wt. % of pancrelipase and from about 70 to about 96% of at least one carrier; or from about 5 to about 19 wt. % of pancrelipase and from about 71 to about 95% of at least one carrier, or from about 10 to about 15 wt. % of pancrelipase and from about 75 to about 90% of at least one carrier, wherein each said wt. % is based on the total weight of the uncoated beads.

In one further embodiment of the invention, the beads that are enterically coated comprise: from about 10 to about 15 wt. % of pancrelipase and from about 80 to about 85% of at least one carrier, wherein each said wt. % is based on the total weight of the uncoated beads.

In the present invention, low pancrelipase content powder blends are disclosed that have high content uniformity and very low segregation while also showing excellent flowability. These blends are particularly suitable for producing the low or diluted pancrelipase beads.

For the present invention, the digestive enzyme beads include any kind of particulate. The term "bead" includes granules, tablets, spheres, minitablets, microtablets, microparticles, microspheres, minimicrospheres, microcapsules, micropellets, as well as particles up to about 5 mm in diameter. The bead may be any suitable particle size or shape. For example, the beads can have a particle size range of about 50 μm to about 5,000 μm or of about 50 μm to about 2,000 μm, they can have a nominal (e.g., mean) particle diameter in the range of about 2 to about 5 mm, or of less than about 2 mm for example of about 0.5 to about 2 mm. Beads may have diameters for example of about 0.7 to about 1.6 mm, or of about 0.7 to about 1.25 mm, or of about 0.7 to about 1.25 mm. "Minimicrospheres" having the smallest median particle size of about 1.15 mm or "microtablets" having highest median particle size at about 2.63 mm are also suitable for the present process. The beads can have an average particle size of less than about 800 μm, preferably less than about 500 μm, preferably of about 400 μm to about 600 μm or of about 250 μm to about 500 μm. These beads may have a volume diameter (d(v,0.1) (defined as the diameter where 10% of the volume distribution is below this value and 90% is above this value) of not less than 400 μm and a volume diameter d(v,0.9) (defined as the diameter where 90% of the volume distribution is below this value and 10% is above this value) of not more than 900 μm.

All these diluted digestive enzymes beads, more particularly pancrelipase enzymes beads, suitable for the preparation of pharmaceutical products may be enterically coated beads. In embodiments where there is an enteric coating, this coating acts as a barrier, protecting the drug substance from the acidic environment of the stomach and substantially prevents the release of the medication before it reaches the small intestine (i.e., the release of enzyme in the stomach is less than about 10 to about 20% of the total amount of enzyme in the composition). Suitable combinations of enteric coating compositions with other coating compositions can be used to provide the desired type of control over drug release or therapeutic effects. The enteric coating includes at least one enteric polymer and further excipients. The phrase "enteric polymer" means a polymer that protects the digestive enzymes from gastric contents, for example a polymer that is stable at acidic pH, but can break down rapidly at higher pH or a polymer whose rate of hydration or erosion is slow enough to ensure that contact of gastric contents with the digestive enzymes is relatively minor while it is in the stomach, as opposed to the remainder of the gastro-intestinal tract.

The compositions and dosages forms of the invention comprise at least one digestive enzyme.

The term "digestive enzyme" used herein denotes an enzyme in the alimentary tract which breaks down the components of food so that they can be taken or absorbed by the organism. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-galactosidase, isomaltase, and mixtures thereof. They are obtained through extraction from the pancreas or pancreatic juices or produced artificially or obtained from sources other than pancreas such as from microorganisms, bacteria, mold, fungi, plants or other animal tissues, genetically modified microorganisms, fungi or plants.

The terms "pancrelipase" or "pancrelipase enzymes" or "pancreatin" denotes a mixture of several types of enzymes, including amylase, lipase, and protease enzymes, or mixtures thereof having pancreatic origin. Pancrelipase is commercially available, for example from Nordmark Arzneimittel GmbH, Scientific Protein Laboratories LLC or Sigma Aldrich; and similar extracts from porcine, bovine or other mammalian sources may be used.

The term "lipase" denotes an enzyme that catalyzes the hydrolysis of lipids to glycerol and simple fatty acids. Examples of lipases suitable for the present invention include, but are not limited to animal lipases (e.g., porcine lipases), bacterial lipases (e.g., Pseudomonas lipase and/or Burkholderia lipase), fungal lipases, plant lipases, recombinant lipases (e.g., produced via recombinant DNA technology by a suitable host cell, selected from any one of microorganisms, bacteria, yeast, fungi, plants, insects or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), synthetic lipase, chemically-modified lipase, and mixtures thereof. The term "lipids" broadly includes naturally occurring molecules including fats, waxes, sterols, fat-soluble vitamins (such as vitamins A, D, E and K), monoglycerides, diglycerides, triglycerides, phospholipids, etc.

The term "amylase" refers to glycoside hydrolase enzymes that break down starch, for example α-amylases, β-amylases, γ-amylases, acid α-glucosidases, salivary amylases such as ptyalin, etc. Amylases suitable for use in the present invention include, but are not limited to animal amylases, bacterial amylases, fungal amylases (e.g., *Aspergillus* amylase, for example, *Aspergillus oryzae* amylase), plant amylases, recombinant amylases (e.g., produced via recombinant DNA technology by a suitable host cell, selected from any one of microorganisms bacteria, yeast, fungi, plants, insects or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, and mixtures thereof.

The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism. Non-limiting examples of proteases suitable for use in the present invention include serine proteases, threonine proteases, cysteine proteases, aspartic acid proteases (e.g., plasmepsin) metalloproteases and glutamic acid proteases. In addition, proteases suitable for use in the present invention include, but are not limited to animal proteases, microbial proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases, which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, and mixtures thereof.

The pancrelipase enzymes of the compositions or oral dosage forms of the compositions of the present invention can include one or more lipases (i.e., one lipase, or two or more lipases), one or more amylases (i.e., one amylase, or two or more amylases), one or more proteases (i.e., one protease, or two or more proteases), as well as mixtures of these enzymes in different combinations and ratios. In certain embodiments, the ratio of amylase/lipase activities in the compositions can range from about 1 to about 10, such as from about 2.38 to about 8.75 (e.g., determined by enzymatic assays performed according to USP protocols). In yet another embodiment, the ratio of protease/lipase can range from about 1 to about 8, such as from about 1.86 to about 5.13 (determined by enzymatic assays performed according to USP protocols). In still other embodiments, the ratio of amylase/lipase activities is about 1, about 2, about 3, about 4, about 5, about 6, about 7, about 8, about 9, or about 10.

Lipase activities in the compositions or oral dosage forms of the present invention can be from about 500 to about 5,000 USP units, preferably from about 750 and about 3,000 USP units. In one embodiment of the invention, the lipase activity can range from about 675 to about 825 USP units, the amylase activity from about 1,600 to about 6,575 USP units, and the protease activity from about 1,250 to about 3,850 USP units.

The carrier(s) is/are used in tabletting to increase the bulk of the tablet to a practical size for compression. These ingredients used in the beads of the present invention have the characteristics of excellent carriers for dry blends providing blend flowability and workability and preventing segregation, and provide pancrelipase content uniformity. A well defined particle size distribution is relevant to provide outstanding flow and mixing properties. Moreover the carrier must have low residual moisture content (low "free water" content).

The carrier may be selected from the group consisting of polyols, sugars, sugar alcohols, cellulose, calcium phosphate salts, and amino acids. More specifically, in certain embodiments of the invention the carrier is selected from the group consisting of microcrystalline cellulose, trehalose, inositol, L-proline in anhydrous form, anhydrous dibasic calcium phosphate, lactose anhydrous, lactose monohydrate, isomalt, mannitol and mixtures thereof, as well as other carriers known in the art.

In a particular embodiment of the invention, the carrier has a large particle size. The term "large size" is defined to be greater than 100 µm; particularly from about 100 µm to about 300 µm, and more particularly from about 160 µm, about 180 µm, about 280 µm, inclusive of all ranges and subranges therebetween, e.g., about 160 µm to about 280 µm, about 160 µm to about 180 µm, about 180 µm, to about 280 µm.

Microcrystalline cellulose is a form of cellulose obtained by spray-drying washed, acid-treated cellulose. It is available in several grades that range in average particle size from 20-100 µm. In addition, microcrystalline cellulose having a mean particle size greater than 100 µm (large particle size microcrystalline cellulose) is also available; e.g., large particle size microcrystalline cellulose of about 160 µm or about 180 µm.

In one particular embodiment of the invention the carrier is large particle size microcrystalline cellulose.

The large particle size microcrystalline cellulose may have a moisture content equal to or less than 5%, nominal mean particle size of about 160 µm, mesh size 38: amount retained ≤1.0%, mesh size of 94: amount retained ≤50.0%, mesh size 300: amount retained ≤70.0%. It has preferably a LoD (loss on drying) of not more than 3.8%.

In another embodiment, the large particle size microcrystalline cellulose may have a moisture content equal to or less than 5%, nominal mean particle size of about 180 µm, mesh size 60: amount retained ≥10.0%, mesh size of 100: amount retained ≥50.0%. It has preferably LoD not more than 1.5%.

In a further embodiment, the microcrystalline cellulose having a moisture content equal to or less than 5%, nominal mean particle size of about 50 µm, mesh size 60: amount retained ≤1.0%, mesh size of 200: amount retained ≤30.0% is used in very low amount (such as about 5.8% by weight of total carrier weight) in admixture with the microcrystalline cellulose having a larger particle size.

Another suitable carrier may be hydrated or anhydrous trehalose (α-D-glucopyranosyl-α-D-glucopyranoside, which is a naturally occurring, non-reducing disaccharide. It is found, for example, in the blood of insects, in fungi, in certain yeasts, and in certain drought-resistant plants. It can be manufactured by fermentation of certain strains of yeast. Trehalose is sweet tasting, and has been suggested for use as a sweetener having reduced cariogenicity in chewing gum and the like. Trehalose is normally manufactured and used as the crystalline dehydrate. Amorphous particulate trehalose may have particle size in the range of about 180 µm to about 280 µm. A particular trehalose used according to the invention is trehalose in its 9.5% dihydrate form, having a low hygroscopic profile. The marketed trehalose used in one embodiment of the present invention is Trehalose G.

Other examples of carriers suitable for use in the present invention are inositol, L-proline in anhydrous form, anhydrous dibasic calcium phosphate (LoD of 0.1-0.2%), lactose, anhydrous lactose (monohydrate with LoD: 4.5-5.5%), and isomalt (LoD of 0.12%).

In the compositions of present invention one single carrier may be used but also a combination of two or more different carriers may be used.

In one embodiment of the invention, only large particle size microcrystalline cellulose is used.

In another embodiment, a binary blend of microcrystalline cellulose and trehalose is used.

In a further embodiment, a blend of two celluloses is used.

In another embodiment of the present invention, the carrier is a mixture of 1:1 w/w of microcrystalline cellulose having a moisture content equal to or less than 5%, nominal mean particle size of about 160 µm, mesh size 38: amount retained ≤1.0%, mesh size 94: amount retained ≤50.0%, mesh size 300: amount retained ≤70.0%, and trehalose.

In another embodiment of the present invention, the carrier is a mixture of 1:1 w/w of microcrystalline cellulose having a moisture content equal to or less than 5%, nominal mean particle size of about 180 µm, mesh size 60: amount retained ≥10.0%, mesh size of 100: amount retained ≥50.0%, and trehalose.

In another embodiment, the carrier is a mixture of 1:1 w/w of two microcrystalline celluloses (MC); one MC having a moisture content less than 5%, nominal mean particle size of about 160 µm, mesh size 38 amount retained ≤1.0%, mesh size of 94, amount retained ≤50.0%, mesh size 300: amount retained ≤70.0%, and the other MC having a moisture content equal to or less than 5%, nominal mean particle size of about 180 µm, mesh size 60 amount retained ≥10.0%, mesh size of 100, amount retained ≥50.0%.

In another embodiment the carrier is a mixture of 16:1 w/w of two microcrystalline celluloses; respectively the first MC having moisture content less than 5%, nominal mean particle size of about 160 µm, mesh size 38: amount retained ≤1.0%, mesh size of 94: amount retained ≤50.0%, mesh size 300: amount retained ≤70.0%, and the other MC having a moisture content equal to or less than 5%, nominal mean particle size of about 50 µm, mesh size 60: amount retained ≤1.0%, mesh size of 200: amount retained ≤30.0%.

The blends comprising pancrelipase and carrier/s and optionally further excipients must have excellent flow properties and consistent particle size. The flow characteristics should enable the loading of the tablet die without difficulty. A sieving procedure can be incorporated to ensure a more controlled even particle size. This is important to guarantee thorough mixing of the components and final homogeneity of the blend.

In addition to the digestive enzymes and the carrier, the beads of the compositions or oral dosage forms of the present invention can further comprise one or more pharmaceutically acceptable excipients. In one embodiment of the invention the amount of excipient is about 5% w/w of the blend. The term "excipients" includes other pharmaceutically acceptable ingredients added to the active component(s) of a composition (e.g., the diluted digestive enzymes) in order to improve processing, stability, palatability, etc. Non-limiting examples of suitable excipients include pharmaceutically acceptable binders, stabilizers, disintegrants, lubricants, glidants, diluents, dyes (coloring agents), stabilizers and mixtures thereof etc. It will be appreciated by those skilled in the art of pharmaceutical formulations that a particular excipient may carry out multiple functions in the composition. The excipients can have a low moisture content, in particular the excipients should have very low "free water" content (less than 15%, less than 10%, about 3% or less). The "free water" is the unbound water.

Non-limiting examples of suitable binders and diluents include starches, modified celluloses (e.g., hydroxypropylcellulose, carboxymethylcellulose sodium), alginic acid, polyvinyl pyrrolidone (povidone), amino acids (proline) and mixtures thereof.

Non-limiting examples of suitable disintegrants include dibasic calcium phosphate, dibasic calcium phosphate dihydrate, tribasic calcium phosphate, alginic acid, hydroxypropylcellulose (such as L-HPC), carboxymethylcellulose calcium, carboxymethylcellulose sodium, cross-linked carboxymethylcellulose sodium, swellable ion exchange resins, alginates, formaldehyde-casein, cellulose, croscarmellose sodium (e.g., Ac-Di-Sol®), crospovidone (e.g., cross-linked polyvinyl pyrrolidone) (e.g., Kollidon®, CL, Polyplasdone® XL, Polyplasdone® XL-10), sodium carboxymethyl starch, sodium starch glycolate (e.g., Explotab®, Explotab® CV), starches (corn starch, rice starch, maize starch), and mixtures thereof. These disintegrants have low amount of moisture content (LoD), preferably less than 15%, even more preferably less than 10%, for example croscarmellose sodium may have LoD of less than 15%, sodium starch glycolate may have LoD of about 7-10%, maize starch may have LoD of less than 15%.

Non-limiting examples of suitable lubricants include calcium stearate, magnesium stearate, sodium stearyl fumarate, stearic acid, zinc stearate, talc, waxes, Sterotex®, Stearowet®, and mixtures thereof.

Non-limiting examples of suitable glidants include colloidal silicon dioxide, talc, and mixtures thereof.

Non-limiting examples of suitable stabilizers include trehalose, proline, dextran, maltose, sucrose, mannitol, polyols, silica gel, aminoguanidine, pyridoxamine, and mixtures thereof.

Dyes and coloring compounds such as inorganic or organic pigments may be also added to the blend. Non limiting examples are metal oxides, such as $TiO_2$, $Fe_2O_3$/$Fe_2O$ $3H_2O$, caramel, malt extract (Corocon®), sugar cane (brown sugar). The LoD of metal oxides is less than 1%.

One or more of the excipients used in the present invention can function as a desiccant to further stabilized the composition. Suitable excipients useful as desiccants include any pharmaceutically acceptable excipient that binds water tightly, or reduces the water activity of a composition. For example, the composition of the present invention can include about 1-4% silica gel, or about 2.5% silica gel, anhydrous proline or trehalose.

In one embodiment of the present invention the enterically coated beads comprise about 15 wt. % of pancrelipase, about 80% of the carrier and about 5% of further excipients, wherein each said wt. % is based on the total weight of the uncoated beads.

In another embodiment the enterically coated beads comprise about 10 wt. % of pancrelipase, about 85% of the carrier and about 5% of further excipients, wherein each said wt. % is based on the total weight of the uncoated beads.

The diluted pancrelipase beads of the invention may have an enteric coating comprising about 10 to about 20 wt. % of at least one enteric polymer wt. % based on the total weight of the coated beads. Non-limiting examples of gastro-resistant—enteric polymers are cellulose acetate phthalate, hydroxypropylmethylcellulose phthalate, hydroxypropylmethylcellulose acetate succinate, polyvinylacetate phthalate, copolymers of methacrylic acid, esters of methylmethacrylate, and shellac. These polymers are commercially available with different brand names, such as: Cellacefate® (cellulose acetate phthalate), Eudragit® L100, S100, L30D, FS30D, L100-55 (copolymers of methacrylic acid), Aquateric® (cellulose acetate phthalate), Aqoat® (hydroxypropyl methylcelluloacetate succinate), HP55® (hydroxypropyl methylcellulose phthalate).

The coating may further comprise stabilizing agents. Other optional ingredients of the coating are plasticizers, anti-sticking agents, inorganic compound (such as talc, magnesium stearate, colloidal silicon dioxide and combinations thereof); further optionally a low viscosity ethylcellulose). Non-limiting examples of suitable plasticizers include triacetin, tributyl citrate, triethyl citrate, acetyl tri-n-butyl citrate, diethyl phthalate, dibutyl sebacate, polyethylene glycol, polypropylene glycol, castor oil, acetylated mono- and di-glycerides, cetyl/myristil alcohol, and mixtures thereof. The preferred plasticizer is a non-phthalate plasticizer or mixtures thereof of two or more (preferably two) of the listed plasticizers in any combinations.

The inorganic material can include, for example, silicon dioxide, sodium salts, calcium salts, magnesium salts, aluminum salts, aluminum hydroxides, calcium hydroxides magnesium hydroxides, talc, and combinations thereof. In one embodiment, this material is talc.

Depending on the intended use of the composition, the ratio of the enteric polymer and the at least one inorganic material may be in a range of from about 10:1 to about 1:60 by weight. In another embodiment, the ratio of the enteric polymer and the at least one inorganic material ranges from about 8:1 to about 1:50 by weight. In another embodiment, the ratio of the enteric polymer and the at least one inorganic material ranges from about 6:1 to about 1:40 by weight. The ratio of the enteric polymer and the at least one inorganic material may range from about 5:1 to about 1:30 by weight, preferably the ratio of the enteric polymer and the at least one inorganic material ranges from about 4:1 to about 1:25 by weight or from about 4:1 to about 1:9 by weight. The ratio of the enteric polymer and the at least one inorganic material may range from about 10:4 to about 10:7 by weight. The inorganic material of the enteric coating comprises about 1 to about 10% by weight of the weight of the total weight of the particles. In another embodiment the inorganic material comprises about 3, about 5, about 7, or about 10% by weight of the particles. When the inorganic material is talc, it comprises about 20 to about 60% of the dry coating weight, for example about 20%, about 25%, about 30%, about 35%, about 40%, about 45%, about 50%, about 55%, or about 60% of the dry coating weight (inclusive of all ranges, sub-ranges, and values therebetween). In a preferred embodiment, the inorganic compound is talc. In still another particular embodiment, the dry coating of the particles comprises about 31% talc.

In one embodiment of the invention, the coating comprises about 10 to about 20% of a least one enteric polymer, about 4 to about 10% of a least one inorganic compound, and about 1 about 2% of at least one plasticizer (based on the total weight of the particles). For example, the coating can comprise about 10 to about 20% of hydroxypropylmethylcellulose phthalate, about 4 to about 10% of talc, and about 1 to about 2% of triethyl citrate (based on the total weight of the particles).

The coating can be applied to the diluted digestive enzyme-containing beads as a solution of the enteric polymer (and optionally a suspended inorganic material) in an organic solvent such as an alcohol (e.g. ethanol, isopropyl alcohol), a ketone (e.g. acetone), methylene chloride, or mixtures thereof (e.g. mixtures of acetone and ethanol). In a preferred embodiment the hydroxypropylmethylcellulose phthalate is the enteric polymer and acetone is the solvent.

The coated diluted digestive enzyme-containing beads can then be formulated into any suitable oral dosage form. The preferred dosage forms of the present invention are the capsules. The capsules themselves can be comprised of any conventional biodegradable material known in the art, for example, gelatin, polysaccharides such as pullulan, or modified cellulosic materials such as hydroxypropylmethylcellulose. In order to improve the stability of the stabilized digestive enzymes, the capsule can be dried prior to filling, or a capsule comprised of a low moisture content material can be selected. In a preferred embodiment, the capsule shell is comprised of hydroxypropylmethylcellulose and has a water content of about 5% or less, for example about any of 4% or less, 2% or less, or 2-5%, or 3-5%, preferably having a water content of less than about 3% even preferably less than 2%.

The term "moisture content", also referred to as "water content", means the amount of water that a composition contains. For compositions that do not change volume with changing moisture content, the moisture content can be expressed volumetrically (i.e., by volume) as the ratio of the mass of moisture to the dry volume of the material. For compositions that change volume with changing moisture content, the moisture content can be expressed gravimetrically (i.e., by weight) as the mass of water removed upon drying per unit dry mass of the specimen. Determination of moisture content can be achieved by any of the conventional methods known in the art. For example, the moisture content can be determined by chemical titration, such as Karl Fischer titration, in which a sample is dissolved in an electrochemical titration cell. Water from the sample is consumed in an electrochemical reaction whose endpoint is measured potentiometrically, thereby providing a direct measure of the amount of water in the sample. Alternatively, relatively simple thermogravimetric methods may be used such as "Loss on Drying" (LoD), in which the mass of a sample is measured prior to, and after controlled drying. The loss of mass after drying is attributed to loss of moisture. Commercially available moisture analyzers (e.g., available from Mettler Toledo, Sartorius AG, etc.) can also be used to determine moisture content.

The moisture content of the ingredients and of the compositions or oral dosage forms of the present invention can be measured by any suitable method known in the art, for example LoD, or thermogravimetric analysis. LoD is the preferred method.

The compositions or oral dosage forms of the present invention, comprising at least one digestive enzyme, may have a water activity of about 0.6 or less, about 0.5 or less, about 0.4 or less, about 0.3 or less, about 0.2 or less, or about 0.1 or less, inclusive of all ranges and subranges therebetween (i.e., any of about 0.5 to about 0.6, about 0.4 to about 0.6, about 0.3 to about 0.6, about 0.2 to about 0.6, about 0.1 to about 0.6, about 0.4 to about 0.5, about 0.3 to about 0.5, about 0.2 to about 0.5, about 0.1 to about 0.5, about 0.3 to about 0.4, about 0.2 to about 0.4, about 0.1 to about 0.4, about 0.2 to about 0.3, about 0.1 to about 0.3, about 0.1 to about 0.2, etc.). Compositions or oral dosage forms of the present invention, maintained at a low water activity, have been found to be substantially more stable compared to conventional digestive enzymes compositions maintained at higher water activity levels.

Water activity, also referred to as "aw", is the relative availability of water in a substance. As used herein, the term "water activity" is defined as the vapor pressure of water in a sample divided by the vapor pressure of pure water at the same temperature. Pure distilled water has a water activity of exactly one. Water activity is temperature dependent. That is, water activity changes as the temperature changes. In the present invention, water activity is measured at a temperature ranging from about 0° C. to about 50° C., preferably from about 10° C. to about 40° C.

The water activity of a product can be determined by measuring the relative humidity of the air surrounding the sample at equilibrium. Accordingly, measurement of water activity in a sample is typically carried out in an enclosed (usually insulated) space where this equilibrium can take place. At equilibrium, the water activity of the sample and the relative humidity of the air are equal, and therefore a measurement of the equilibrium relative humidity (ERH) of the air in the chamber provides a measure of the water activity of the sample. At least two different types of water activity instruments are commercially available. One type of water activity instruments uses chilled-mirror dew point technology (e.g., AquaLab® water activity meters available from Decagon Devices, Inc.) while others measure relative humidity with sensors that change electrical resistance or capacitance (e.g., water activity meters available from Rotronic®). The water activity of the compositions or oral dosage forms of the present invention can be measured by any suitable method known in the art.

The compositions or dosage forms of the present invention, comprising at least one stabilized digestive enzyme show no loss of enzymatic activity after three months of accelerated stability testing. The composition or dosage form may exhibit a loss of enzyme activity of no more than about 25%, no more than about 20%, no more than about 15%, no more than about 12%, no more than about 10%, no more than about 8%, or no more than about 5%, after six months of accelerated stability testing.

The term "accelerated stability testing" or "accelerated storage testing" refers to test methods used to simulate the effects of relatively long-term storage conditions on enzyme activity, which can be carried out in a relatively short time. Accelerated stability testing methods are known in the art to be a reliable alternative to real-time stability testing, and can accurately predict the shelf life of biological products. Such "accelerated stability testing" conditions are known in the art and are in accordance with the International Conference for Harmonization of Technical Requirements for Registration of Pharmaceuticals for Human Use: Stability Testing of New Drug Substances and Products Q1A, herein incorporated by reference in its entirety.

After storage (or periodically during storage) the enzyme activity of the samples can be tested using conventional methods for assaying digestive enzyme activity (e.g., U.S. Pharmacopoeia, Pancrelipase: Assay for lipase activity; herein incorporated by reference in its entirety).

The compositions of the present invention, and dosage forms comprising the compositions of the present invention, have high stability compared to conventional digestive enzymes (e.g., pancrelipase) compositions and dosage forms and deliver the clinically useful amount of digestive enzyme to a patient, comprising infants or newborns.

The composition or dosage form (e.g., tablet or capsule) of the present invention can be stored in any suitable package. For example, the package can be a glass or plastic jar with a threaded or press-fit closure. Alternatively, the compositions or dosage forms of the present invention can be packaged as a unit dosage form in "blister packs". Improved stability of the digestive enzyme compositions or dosage forms can be provided by providing a moisture-proof seal, and/or a moisture-proof package. Non-limiting examples of suitable moisture-proof packages include glass jars, plastic jars incorporating moisture barrier resins or coatings, aluminized plastic (e.g., Mylar) packaging, etc. The term "moisture-proof" refers to a package which has permeability to water of less than about 0.5 mg water per $cm^3$ of container volume per day.

Containers (e.g., bottles) can be closed with any suitable closure, especially closures which minimize the ingress of moisture during storage. For example, the compositions or dosage forms of the present invention can be thermosealed aluminum liners and polyethylene foam cap liners. In order to ensure package integrity and minimize moisture ingress during storage, sealed packages containing the compositions or dosage forms of the present invention can be leak-tested after dispensing the composition or dosage form of the present invention and sealing the package. For example, the sealed packages can be tested by applying a controlled vacuum to the closure, and detecting the decrease in vacuum over time. Suitable leak-testing equipment includes those manufactured by Bonfiglioli (e.g., model LF-01-PKV or model PKV 516).

Packages containing the compositions or dosage forms of the present invention can also contain a desiccant (i.e., a substance which absorbs, reacts with, or adsorbs water) capable of reducing the humidity inside the package, for example a desiccant, capable of "scavenging" moisture from the atmosphere sealed inside the package. Non-limiting examples of suitable desiccants that can be placed inside such packages include zeolites (e.g., molecular sieves such as 4 A molecular sieves), clay (e.g., montmorillonite clay), silica gel, or combinations thereof. In one embodiment, the desiccant comprises molecular sieves.

In addition, it is common practice when packaging oral pharmaceutical unit doses to add a "plug" of a cellulosic material, such as cotton, into the top of the container to fill the empty space at the top of the container, thereby minimizing movement of the contents. Cellulosic materials are somewhat hygroscopic, and can act as a "reservoir" of moisture inside the package. Accordingly, in the present invention, no cellulosic or cotton "plug" is added. One embodiment of the present invention is the process of preparation of the composition and dosage form with low and uniform pancrelipase content that comprises the following steps:

a) mixing the at least one digestive enzyme and at least one carrier or mixture thereof and optional further excipients to form a mixture; the mixing is carried out under mild condition (such as manual grinding in mortar); high energy milling should be avoided to reduce the risk of lipase activity reduction;

b) direct compressing the mixture into beads;

c) coating the beads with a solution comprising at least one enteric polymer.

The process further comprises the following steps:

d) preparing the dosage forms with the coated beads, such as filling capsules with the coated beads;

e) packaging the dosage forms.

It is highly relevant that all process steps are conducted under strict control of environmental moisture, which should be kept at a very low level; for examples the absolute moisture of incoming air during coating should be kept at values of about 2 to about 3 g/kg, relative humidity during step d) should be less than 40%. Moreover, all ingredients of the blend and of the coating should also have very low moisture content (or preferably less than about 15, or less than about 10%, or less than about 5%, or less than about 3%). The capsule shell should also have low moisture content (less than about 5%, preferably less than about 3%) to minimize water transfer to the product. The packaging configuration should also be carefully chosen in order minimize water permeability. Only under these circumstances do the final diluted digestive enzyme compositions or dosage forms have prolonged storage stability.

Several dosage formulations can be made in which different dimensions of the tablets are obtained. A pancrelipase blend containing the pancrelipase, the carrier(s) and the additional excipients can be tabletted for example using round 2 mm diameter beveled punches, or with round 1.5 mm diameter, 1.2 mm radius of curvature punches to produce microtablets with different dimensions. The blend may be tabletted using compression parameters suitable to obtain pancrelipase minitablets or microtablets. For example, diluted pancrelipase microtablets can be produced according to this invention with weight of about 2 mg to about 4 mg, preferably from about 2.6 to about 3.64 mg, with friability lower than about 2.5% p/p (USP method) and with thickness from about 1.5 to about 2.0 mm.

One embodiment of the present invention provides a method of treating or preventing a condition or disorder associated with digestive enzyme deficiency in a patient, comprising administering the pharmaceutical composition or dosage form of the present invention to a patient (e.g., a mammal such as a human) in need thereof.

In another embodiment, the invention provides a method of treating or preventing a disorder or condition associated with digestive enzyme deficiency, comprising administering the composition or dosage form of the present invention to a patient in need thereof, wherein the composition or dosage form comprises, in addition to the digestive enzymes, at least one proton pump inhibitor, or one antacid, or other medicament which increases GI pH. In still another embodiment, the present invention provides a method of treating or preventing a disorder or condition associated with digestive enzyme deficiency, comprising administering a composition or dosage form of the present invention, in combination with a dosage form comprising at least one proton pump inhibitor, one antacid, or other medicament which increases GI pH.

Disorders or conditions that can be treated with the composition or dosage forms of the present invention include conditions in which the patient has no or low levels of digestive enzymes or in which patients require digestive enzyme supplementation. For example, such conditions can include exocrine pancreatic insufficiency, cystic fibrosis, chronic pancreatitis, other pancreatic diseases (e.g., hereditary, post-traumatic and allograft pancreatitis, hemochromatosis, Shwachman syndrome, lipomatosis, or hyperparathyroidism), side-effects of cancer or cancer treatment, side-effects of surgery (e.g., gastrointestinal bypass surgery, Whipple procedure, total pancreatectomy, etc.) or other conditions in which pancreatic enzymes cannot reach the intestine, poor mixing (e.g., Billroth II gastrectomy, other types of gastric bypass surgery, gastrinoma, etc.), side effects of drug treatments such as treatment with metformin or those drugs used to treat the symptoms of HIV and autoimmune diseases such as diabetes in which the pancreas may be compromised, obstruction (e.g., pancreatic and biliary duct lithiasis, pancreatic and duodenal neoplasms, ductal stenosis), malabsorption associated with celiac disease, food allergies and aging.

Particularly relevant for the purpose of present invention is the treatment of newborns and infants in need of treatment thereof with the diluted composition or dosage form of the present invention.

The term "pharmaceutically effective amount" refers to an amount of composition of the invention or dosage form thereof, as disclosed herein, effective in reducing or ameliorating conditions or symptoms associated with pancreatic enzyme insufficiency in a patient.

In one embodiment of the invention, an effective amount of the compositions or dosages forms herein disclosed are administered in the treatment of pancreatic enzyme replacement therapy (PERT) in CF (cystic fibrosis) newborns or infants with symptomatic or confirmed pancreatic insufficiency or exocrine pancreatic insufficiency. The compositions or dosage forms are administered for improving coefficient of fat absorption (CFA).

From the foregoing description and the experiments disclosed herein, it can be seen that the present invention provides several important advantages. The described invention provides diluted pancrelipase compositions and dosage forms characterized by high content uniformity and stability, and the composition and dosage forms herein are therefore suitable for use with infants and newborns who need low doses of pancreatic enzymes.

It is to be understood that both the general description and the detailed description herein are exemplary, but not restrictive of the invention, and that all embodiments can naturally be combined with one another.

EXAMPLES

Methods

Dissolution test. a) Acid stage medium (pH 1.2): Place 2.00 g of sodium chloride in 800 mL purified water and stir until complete solubilization. Add 7 mL 37% HCl and mix. Adjust the pH of the solution to 1.20±0.05 with 1 N HCl or 1 N NaOH. Dilute to 1000 mL with purified water; check the pH and adjust to 1.20±0.05 with 1 N HCl or 1 N NaOH, if needed. b) Enteric stage medium (pH 6.0): Place 9.20 g monobasic potassium phosphate and 2.00 g sodium chloride in 800 mL purified water and stir until complete solubilization. Adjust the pH of the solution to 6.00±0.05 with 1 N NaOH. Dilute to 1,000 mL with purified water; check the pH and adjust to 6.00±0.05 with 1 N HCl or 1 N NaOH, if needed.

The measurement of lipolytic activity is carried out using a method based on the compendia procedure of lipase assay described in the pancrelipase USP monograph, which is based on the titration, by means of pH-stat method, of the free fatty acids formed from the hydrolysis of esterified fatty acids in the substrate used (olive oil). It is based on the following principle: lipase catalyses the hydrolysis of the triglycerides which leads to the formation of free fatty acids (FFA). The titration of the formed FFA according to time provides for the determination of the enzymatic activity of lipase, which can be expressed in units: 1 U=1 mole of formed FFA per minute. The reaction occurs by maintaining a steady pH value through an experimental system that provides for the addition of NaOH (titrant) when the pH value changes compared to a fixed value (pHstat method). The quantity of added titrant according to time corresponds to the quantity of FFA formed by the lipase action on the triglycerides. Provided that the procedure is carried out with a suitable quantity of substrate and under experimental conditions where the enzyme is stable, linear kinetics for the FFA formation according to time can be obtained. The curve slope {added titrant=f (volume (mL)/time (minutes))} gives the lipase enzymatic activity.

The measurement of proteolytic activity is carried out according to the compendia procedure described in the pancrelipase USP monograph.

Example 1. Pancrelipase-Carrier Blends Compatibility

Binary blends of pancrelipase and carrier are prepared by mixing to ascertain the stability of the pancrelipase in presence of said ingredients. This binary blend contains pancrelipase in amount of 60 mg and the carrier in amount of 324 mg; the tested carriers are: microcrystalline cellulose (microcrystalline cellulose C: moisture content equal or less than 5%, nominal mean particle size of 50 µm, mesh size 60: amount retained ≤1.0%, mesh size of 200: amount retained ≤30.0%; marketed as Avicel® PH101), trehalose, lactose monohydrate, isomalt, proline inositol. The samples are packaged in 10 mL PET and glass vials in the absence of desiccant. They are stored under two different conditions: mild storage condition (25° C., 65% relative humidity (RH)) and aggravated storage conditions (40° C., 75% relative humidity). Lipase activity is tested after different periods of storage according to the compendia method described herein.

TABLE 1

Lipase activity of the blends stored at 25° C./65 RH, PET vials (lipase activity of the blends is calculated as % of the lipase activity of the pancrelipase sample)

| | | Storage time | | | |
|---|---|---|---|---|---|
| | Carrier | 0 | 1 week | 2 weeks | 4 weeks |
| Pancrelipase (USP units lipase) | none | 95 | 94 | 90 | 80 |

TABLE 1-continued

Lipase activity of the blends stored at 25° C./65 RH, PET vials
(lipase activity of the blends is calculated as % of the lipase
activity of the pancrelipase sample)

|  |  | Storage time | | | |
|---|---|---|---|---|---|
|  | Carrier | 0 | 1 week | 2 weeks | 4 weeks |
| Pancrelipas | Cellulose microcrystalline C | 98 | 100 | 99 | 103 |
| Pancrelipase | Trehalose | 100 | 99 | 99 | 98 |
| Pancrelipase | Lactose monohydrate | 99 | 100 | 98 | 98 |
| Pancrelipase | Anhydrous dibasic calcium phosphate | 93 | 98 | 96 | 100 |
| Pancrelipase % | Isomalt | 100 | 98 | 94 | 99 |
| Pancrelipase % | Proline | 100 | 101 | 99 | 87 |
| Pancrelipase % | Inositol | 100 | 97 | 96 | 103 |

TABLE 2

Lipase activity of the blends stored at 25° C./65 RH, glass vials
(lipase activity of the blends is calculated as % of
the lipase activity of the pancrelipase sample)

|  |  | Storage time | |
|---|---|---|---|
|  | Carrier | 0 | 1 week |
| Pancrelipase (USP units lipase) | None | 95 | 94 |
| Pancrelipase | Cellulose microcrystalline C | 98 | 98 |
| Pancrelipase | Trehalose | 100 | 99 |
| Pancrelipase | Lactose monohydrate | 99 | 97 |
| Pancrelipase | Anhydrous dibasic calcium phosphate | 93 | 102 |
| Pancrelipase | Isomalt | 100 | 97 |

TABLE 3

Lipase activity of the blends stored at 40° C./75 RH, PET vials
(lipase activity of the blends is calculated as % of the lipase activity
of the pancrelipase sample)

|  |  | Storage time | | | |
|---|---|---|---|---|---|
|  | Carrier | 0 | 1 week | 2 weeks | 4 weeks |
| Pancrelipase (USP units lipase) | None | 95 | 96 | 48 | 31 |
| Pancrelipase % | Cellulose microcrystalline C | 98 | 103 | 113 | 113 |
| Pancrelipase % | Trehalose | 100 | 97 | 100 | 106 |
| Pancrelipase % | Lactose monohydrate | 99 | 99 | 106 | 113 |
| Pancrelipase % | Anhydrous dibasic calcium phosphate | 93 | 99 | 106 | 113 |
| Pancrelipase % | Isomalt | 100 | 96 | 102 | 100 |
| Pancrelipase % | Inositol | 100 | 101 | 110 | 106 |

Example 2. Physical Characterization of the Pancrelipase-Carrier Blends

Pancrelipase is blended with one or more carriers and the physical characterization of these mixture is carried out by measuring the density (both bulk and tapped), the Carr index (compactability index), the flowability (flow rate through an orifice is measured as the mass per time flowing from funnel, USP method), the LoD. The summary of the results is reported in Table 4.

TABLE 4

| Batch | Density untapped | Density tapped | % Carr index | Mass flow g/sec (100 g) Ø 10 mm g/s | Ø 15 mm g/s | Ø 20 mm g/s | Ø 30 mm g/s | T = 0 | LoD % 24 h/ room temp; closed vial | 24 h/ room temp; open vial | 72 h/ room temp; closed vial | 72 h/ room temp; open vial |
|---|---|---|---|---|---|---|---|---|---|---|---|---|
| Reference sample[4] | 0.657 | 0.781 | 15.88 | 7.1 | / | / | / | 0.96 | 1.51 | 2.69 | / | / |
| Microcrystalline cellulose C[3] | 0.438 | 0.561 | 21.93 | No flow | No flow | No flow | 20.8 | 3.68 | 4.05 | 4.04 | / | / |
| Microcrystalline cellulose B[2] | 0.423 | 0.500 | 15.40 | 10.4 | / | / | / | 1.09 | 1.59 | 2.12 | / | / |
| Trehalose G | 0.757 | 0.892 | 15.13 | 5.9 | / | / | / | 6.45 | 6.72 | 6.52 | / | / |
| Lactose Monohydrate | 0.549 | 0.632 | 13.13 | 7.1 | / | / | / | 0.43 | 0.71 | 0.87 | / | / |
| L-Proline | 0.512 | 0.581 | 11.88 | 4.5 | / | / | / | 0.43 | / | / | 0.52 | 0.97 |
| Calcium Bibasic | 0.694 | 0.806 | 13.90 | 9.1 | / | / | / | 0.70 | / | / | 0.89 | 1.25 |
| Isomalt | 0.434 | 0.500 | 13.20 | 5.5 | / | / | / | 2.55 | / | / | 2.57 | 2.84 |
| Anhydrous lactose | 0.769 | 0.833 | 7.68 | 4.34 | / | / | / | 0.43 | / | / | 0.51 | 0.86 |
| Microcrystalline cellulose A[1] | 0.434 | 0.515 | 15.73 | 4.34 | / | / | / | 3.89 | 3.92 | 3.96 | / | / |
| Inositol | 0.609 | 0.781 | 22.02 | 6.66 | / | / | / | 0.61 | / | / | 0.45 | 0.93 |
| Microcrystalline cellulose B[2] + C[3] blends (1:1) | 0.442 | 0.549 | 19.49 | No flow | 5.88 | / | / | 2.72 | 2.8 | 2.91 | / | / |
| Microcrystalline cellulose A[1] + C[3] (1:1) | 0.454 | 0.568 | 20.07 | No flow | 14.28 | / | / | 3.36 | 4.17 | 4.17 | / | / |

TABLE 4-continued

| | % Density | | Carr | Mass flow g/sec (100 g) | | | | | LoD % | | | |
|---|---|---|---|---|---|---|---|---|---|---|---|---|
| | | | | Ø 10 mm | Ø 15 mm | Ø 20 mm | Ø 30 mm | | 24 h/ room temp; closed | 24 h/ room temp; open | 72 h/ room temp; closed | 72 h/ room temp; open |
| Batch | untapped | tapped | index | g/s | g/s | g/s | g/s | T = 0 | vial | vial | vial | vial |
| Microcrystalline cellulose C[3] + Trehalose G (1:1) | 0.561 | 0.724 | 22.51 | No flow | 8.33 | / | / | 2.78 | 5.64 | 5.86 | / | / |
| Microcrystalline cellulose C[3] + L-Proline (1:1) | 0.515 | 0.649 | 20.65 | No flow | 12.5 | / | / | 2.39 | 2.19 | 2.18 | / | / |
| Microcrystalline cellulose C[3] + Lactose anhydrous (1:1) | 0.555 | 0.684 | 18.86 | No flow | 3.33 | / | / | 2.07 | 2.27 | 2.15 | / | / |
| Microcrystalline celluloe C[3] + Lactose Monohydrate (1:1) | 0.521 | 0.657 | 20.70 | No flow | 10.0 | / | / | 1.94 | 2.18 | 2.36 | / | / |
| Microcrystalline cellulose C[3] + Calcium bibasic (1:1) | 0.561 | 0.704 | 20.31 | No flow | 10.5 | / | / | 2.1 | 2.5 | 2.65 | / | |
| Microcrystalline cellulose C[3] + Isomalt (1:1) | 0.510 | 0.609 | 16.26 | No flow | 12.5 | / | / | 3.38 | 3.37 | 3.4 | / | / |
| Microcrystalline cellulose C[3] + Inositol (1:1) | 0.531 | 0.675 | 21.33 | No flow | 6.66 | / | / | 2.29 | / | / | 2.06 | 2.27 |

[A]Reference sample: pancrelipase (90%), croscarmellose sodium (3.0%), hydrogenated castor oil (1.0%), colloidal silicone dioxide (0.5%), microcrystalline cellulose (5%) (Avicel® PH101); magnesium stearate (0.5%)

TABLE 5

Types of microcrystalline celluloses

| | Nominal mean particle size (μm) | Particle size analysis: Mesh size | Amount retained % | LoD |
|---|---|---|---|---|
| [1]Microcrystalline cellulose A | 160 | 38 | ≤1 | <5% |
| | | 94 | ≤50 | |
| | | 300 | ≤70 | |
| [2]Microcrystalline cellulose B | 180 | 60 | ≥10.0 | <5% |
| | | 100 | ≥50 | |
| [3]Microcrystalline cellulose C | 50 | 60 | ≤1 | <5% |
| | | 200 | ≤30 | |

Crystalline cellulose A is marketed as Vivapure® 12;
crystalline cellulose B is marketed as Avicel® LM200;
crystalline cellulose C is marketed as Avicel® PH101.

From the above Table 4 it can be evinced that the microcrystalline cellulose C (moisture content equal to or less than 5%, nominal mean particle size of 50 μm mesh size 60: amount retained ≤1.0%, mesh size of 200: amount retained ≤30.0%) has low mass flow which is an indication of critical issues during the direct compression process. To avoid such issues with carriers having low flowability, an additional treatment step (such as wet-granulation) would typically be carried out to increase the mass flow. However, any such additional steps are detrimental to the enzymatic activity of the pancrelipase formulation and therefore should be avoided to reduce the risk of degradation.

Example 3. Hardness Measurements of Tablets of the Pancrelipase-Carrier Blends

Pancrelipase raw material (e.g., received from Nordmark) is mixed with different carriers to form the seven different blends: blend 1: pancrelipase; blend 2: pancrelipase and microcrystalline cellulose B; blend 3: pancrelipase and trehalose; blend 4: pancrelipase and isomalt; blend 5: pancrelipase and calcium bibasic; blend 6: pancrelipase and inositol; blend 7: pancrelipase and microcrystalline cellulose A. Theses blends are tabletted by direct compression and hardness is measured for each sample. The results are reported in FIG. 1.

Suitable hardness values are very crucial since low hardness is critical during the subsequent step of coating process.

Example 4. Preparation of 15% Diluted Pancrelipase Microtablets

Pancrelipase raw material (e.g., received from Nordmark) is mixed with the carrier(s) and the further excipients to form the different blends. Three different blends are prepared.

The first blend (blend 1) contains: 15% pancrelipase, 80% cellulose microcrystalline A (moisture content less than 5%, nominal mean particle size of 160 μm, mesh size 38: amount retained ≤1.0%, mesh size 94: amount retained ≤50.0%, mesh size 300: amount retained ≤70.0%), and 5% excipients (croscarmellose sodium, 3.0%; hydrogenated castor oil, 1.0%; colloidal silicone dioxide, 0.5%; magnesium stearate 0.5%), wherein each said wt % is based on the total weight of the blend.

The second blend (blend 2) contains: 15% pancrelipase, 40% cellulose microcrystalline A (moisture content less than 5%, nominal mean particle size of 160 μm, mesh size 38: amount retained ≤1.0%, mesh size 94: amount retained ≤50.0%, mesh size 300: amount retained ≤70.0%.), 40% trehalose (Trehalose G), 5% excipients (croscarmellose sodium, 3.0%; hydrogenated castor oil, 1.0%; colloidal silicone dioxide, 0.5%, magnesium stearate 0.5%), wherein each said wt % is based on the total weight of the blend.

The third blend (blend 3) contains: 15% pancrelipase, 40% cellulose microcrystalline B (moisture content equal or less than 5%, nominal mean particle size of 180 μm, mesh size 60: amount retained ≥10.0%, mesh size 100: amount retained ≥50.0%.), 40% trehalose (trehalose G), 5% excipients (croscarmellose sodium, 3.0%; hydrogenated castor oil, 1.0%; colloidal silicone dioxide, 0.5%; magnesium stearate 0.5%), wherein each said wt % is based on the total weight of the blend.

Microcrystalline celluloses A and B are defined in Table 5 of Example 3.

The three blends are then tabletted to produce microtablets (1.5×1.5 mm). The microtablets are tested for, lipase activity, disintegration time, LoD; their weight, thickness and friability are also measured on each batch produced (Table 6).

TABLE 6

| Test | μtablet 1 (blend 1) | μtablet 2 (blend 2) | μtablet 3 (blend 3) |
|---|---|---|---|
| Lipase (USP units/mg) | 14.6 | 14.9 | 15.3 |
| Disintegration (min) | 3 | 4 | 3 |
| LoD(%) | 2.3 | 1.8 | 2.7 |
| Weight (mean value) (g) | 0.0034 | 0.0035 | 0.0035 |
| Thickness*(mean value) (mm) | 1.51 | 1.48 | 1.50 |
| Friability* (mean value) (%) | 1.1 | 1.2 | 1.3 |

*USP method (20 g of MT, 30 min at 25 rpm)

The above μtab has high homogeneity in terms of pancrelipase content (CV % below 5%).

Example 5. Preparation of 10% Diluted Pancrelipase Minitablets

Pancrelipase raw material (e.g. obtained from Nordmark) and carrier (microcrystalline cellulose) and excipients (e.g., croscarmellose sodium, hydrogenated castor oil, colloidal silicon dioxide, microcrystalline cellulose, and magnesium stearate) are mixed to form a blend. The composition of the blend is reported in the following table (Table 7), and has a density of 0.75-0.76 g/ml.

TABLE 7

| Component | Kg (theoretical) for 1 batch | % |
|---|---|---|
| Microcrystalline cellulose A | 297.6 | 80 |
| Pancrelipase | 37.2 | 10 |
| Croscarmellose sodium | 11.16 | 3 |
| Hydrogenated castor oil | 3.72 | 1 |
| Colloidal silicon dioxide | 1.86 | 0.5 |
| Microcrystalline cellulose C | 18.6 | 5 |
| Magnesium stearate 0.3-0.4 g/ml | 1.86 | 0.5 |
| Total | 372 | 100 |

Microcrystalline celluloses A and C are defined in Table 5 of Example 3.

The above blend is tabletted using round 2 mm diameter beveled punches; the compression parameters (Table 8) are set to obtain pancrelipase minitablets (MTs) having the following physical characteristics: weight between 0.074 g and 0.086 g, with friability lower than 2.5% p/p (USP method), thickness between 2.0 and 2.4 mm.

TABLE 8

| Compression parameter | 10% pancrelipase MT |
|---|---|
| Tabletting machine speed (rpm) | 20 |
| Forced feeding (rpm) | 20 |
| Average compression force (kN) | about 10 |

TABLE 8-continued

| Compression parameter | 10% pancrelipase MT |
|---|---|
| Average pre compression force (kN) | about 10 |
| Dosing chamber parameters (mm) | 5-5.5 |

4 batches (A-D) of the 10% diluted pancrelipase MTs are produced with these blends; they have the following physical properties (Table 9).

TABLE 9

| | Batch A | Batch B | Batch C | Batch D |
|---|---|---|---|---|
| Weight (mean value) (g) | 0.079 | 0.079 | 0.08 | 0.081 |
| Thickness* (mean value) (mm) | 2.2 | 2.2 | 2.2 | 2.2 |
| Friability* (mean value) (%) | 0.7 | 0.8 | 0.6 | 0.7 |

*USP method (20 g of MT, 30 min at 25 rpm)

Example 6. Content Uniformity of 10% Pancrelipase MTs

The uniformity of the dosage units is demonstrated by measuring the content uniformity. Each batch is prepared as in example 4 and is assayed by measuring the lipase content according to compendia methods for assaying digestive enzymes activity (e.g., United States Pharmacopoeia, Pancrelipase: assay for lipase activity). The assay is repeated 10 times per each batch and the CV % results are reported in Table 10.

TABLE 10

| Batch | Coefficient of variation (%) |
|---|---|
| A | 3.2 |
| B | 2.4 |
| C | 2.0 |
| D | 3.3 |

The MTs prepared show high homogeneity in terms of pancrelipase content. In fact, the requirements for dosage uniformity are met by all assayed batches since the CV % is below 5%.

Example 7. Coating of Diluted Pancrelipase Tablets (μTs and MTs)

The 15% diluted pancrelipase μTs and the 10% diluted pancrelipase MTs (Examples 5 and 6, respectively) are then coated by fluid bed with a coating formulation (having the composition of Table 11) in a coating pan. The coating may be started when the tablets reach temperature of 15-32° C. The composition of the coated particles prepared according to the standard coating method applied for Zenpep® minitabs produces uniform, smooth and homogeneous particles (as analyzed by microscopic examination).

TABLE 11

| Component | % (w/w) |
|---|---|
| Hypromellose phthalate (HP55) | 7.64 |
| Triethyl citrate (TEC) | 0.76 |
| Talc | 3.82 |
| Acetone | 87.78 |
| total | 100.00 |

Hydroxypropylmethylcellulose capsules with very low moisture content are then filled with the coated diluted pancrelipase microtablets.

Example 8. Enzymatic Activity and Dissolution of Enterically Coated Diluted Pancrelipase Formulation HPMC capsules (size 4 white OP/white OP) are filled with diluted enterically coated pancrelipase μTs. The capsules are stored in glass bottle with PP closure-liner, Minipax desiccants. Enzymatic activities are measured on the formulations stored under different conditions (at 25° C. and 60% relative humidity, and at 40° C. and 75% relative humidity) (Tables 13-18). Storage stability of bulk enterically coated diluted pancrelipase microtablets stored at 40° C. and 75% relative humidity in glass bottle with PP closure-liner, Minipax desiccants are also tested (Table 12). The dissolution of the microtablets is also measured.

The enterically coated microtablets 1 (μT1) contains: 15% pancrelipase, 80% cellulose microcrystalline A (moisture content less than 5%, nominal mean particle size of 160 μm, mesh size 38: amount retained ≤1.0%, mesh size 94: amount retained ≤50.0%, mesh size 300: amount retained ≤70.0%), and 5% excipients (croscarmellose sodium, 3.0%; hydrogenated castor oil, 1.0%; colloidal silicone dioxide, 0.5%; magnesium stearate 0.5%), wherein each said wt % is based on the total weight of the uncoated μTs.

The enterically coated microtablets 2 (μT2) contains: 15% pancrelipase, 40% cellulose microcrystalline A (moisture content less than 5%, nominal mean particle size of 160 μm, mesh size 38: amount retained ≤1.0%, mesh size 94: amount retained ≤50.0%, mesh size 300: amount retained ≤70.0%.), 40% trehalose, 5% excipients (croscarmellose sodium, 3.0%; hydrogenated castor oil, 1.0%; colloidal silicone dioxide, 0.5%, magnesium stearate 0.5%), wherein each said wt % is based on the total weight of the uncoated μTs.

The enterically coated microtablets 3 (μT3) contains: 15% pancrelipase, 40% cellulose microcrystalline B (moisture content equal or less than 5%, nominal mean particle size of 180 μm, mesh size 60: amount retained ≥10.0%, mesh size 100: amount retained ≥50.0%.), 40% trehalose, 5% excipients (croscarmellose sodium, 3.0%; hydrogenated castor oil, 1.0%; colloidal silicone dioxide, 0.5%; magnesium stearate 0.5%), wherein each said wt % is based on the total weight of the μTs.

Microcrystalline celluloses A and B are defined in Table 5 of Example 3; the enteric coating composition is the same as the coating of Example 7 (Table 11).

TABLE 12

Stability of bulk enterically coated diluted pancrelipase microtablets (μTs); storage conditions: 40° C. + 75% relative humidity

| Batch | Lipase activity USP units/mg | | |
|---|---|---|---|
| | Time 0 | Time 3 mo | Diff time |
| μT1 (carrier: microcrystalline cellulose A) | 11.5 | 11.2 | 97 |
| μT2 (carrier: microcrystalline cellulose A and trehalose) | 11.7 | 11.7 | 100 |
| μT3 (carrier: microcrystalline cellulose B and trehalose) | 11.5 | 11.4 | 99 |

TABLE 13

Analysis of enterically coated diluted pancrelipase microtablets, μT1 (carrier: microcrystalline cellulose A); storage conditions: 25° C., 60% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 735 | 761 | 754 | 774 |
| | % label claim | 98 | 101 | 101 | 103 |
| | Dff T0 (%) | | 104 | 103 | 105 |
| protease activity (USP units/cps) | 1,250-3,850 USP units/cps | 2,015 | 2,145 | 2,145 | 2,210 |
| amylase activity (USP units/cps) | 1,600-6,575 USP units/cps | 2,600 | 2,665 | 2,665 | 2,795 |
| Pthalic Acid(%) | NMT 1.4% | 0.1 | 0.1 | 0.1 | 0.1 |
| LoD (%) | NMT 5.0% | 2.4 | 0.5 | 0.1 | 0.3 |
| dissolution (%) | NLT 75% 30 min | 84% (RSD 3.6) | 87% (RSD 2.6) | 85% (RSD 2.1) | 83% (RSD 3.0) |
| dissolution (%) × 1.125 | | 95% (RSD 2.9) | 98% (RSD 2.2) | 96% (RSD 1.5) | 94% (RSD 3.0) |
| Weight n = 10 (mg) | | 65 | 65 | 65 | 65 |

TABLE 14

Analysis of enterically coated diluted pancrelipase microtablets μT1 (carrier: microcrystalline cellulose A); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP unis/cps) | 90-110% of label claim 675-825 USP units/cps | 735 | 754 | 754 | 754 |
| | % label claim | 98 | 101 | 101 | 101 |
| | Dff T0 (%) | | 103 | 103 | 103 |
| protease activity (USP units/cps) | 1,250-3,850 USP units/cps | 2,015 | 2,080 | 2,015 | 2,015 |
| amylase activity (USP units/cps) | 1,600-6,575 USP units/cps | 2,600 | 2,665 | 2,600 | 2,795 |
| Pthalic Acid(%) | NMT 1.4% | 0.1 | 0.1 | 0.1 | 0.1 |
| LoD (%) | NMT 5.0% | 2.4 | 0.4 | 0.1 | 0.2 |
| dissolution (%) | NLT 75% 30 min | 84% (RSD 3.6) | 84% (RSD 2.9) | 83% (RSD 2.2) | 82% RD 1.8) |
| dissolution (%) × 1.125 | | 95% (RSD 2.9) | 94% (RSD 2.2) | 96% (RSD 2.3) | 93% (RSD 1.8) |
| Weight n = 10 (mg) | | 65 | 65 | 65 | 65 |

TABLE 15

Analysis of enterically coated diluted pancrelipase microtablets μT2 (carrier: microcrystalline cellulose A and trehalose); storage conditions: 25° C., 76% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 736 | 755 | 762 | 755 |
| | % label claim | 98 | 101 | 102 | 101 |
| | Dff T0 (%) | | 103 | 104 | 103 |
| protease activity (USP units/cps) | 1,250-3,850 USP units/cps | 1,984 | 2,048 | 1,984 | 2,112 |
| amylase activity (USP units/cps) | 1,600-6,575 U USP/cps | 2,496 | 2,688 | 2,880 | 2,816 |
| Pthalic Acid(%) | NMT 1.4% | 0.1 | 0.1 | 0.1 | 0.1 |
| LoD (%) | NMT 5.0% | 1.6 | 0.2 | 0.2 | 0.3 |
| dissolution (%) | NLT 75% 30 min | 84% (RSD 2.0) | 91% (RSD 3.6) | 87% (RSD 2.4) | 86% RD 12.2) |
| dissolution (%) × 1.125 | | 94% (RSD 2.3) | 103% (RSD 3.6) | 98% (RSD 2.5) | 96% (RSD 1.7) |
| Weight n = 10 (mg) | | 64 | 64 | 64 | 64 |

TABLE 16

Analysis of enterically coated diluted pancrelipase microtablets μT2 (carrier: microcrystalline cellulose A and trehalose); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 736 | 755 | 781 | 742 |
| | % label claim | 98 | 101 | 104 | 199 |
| | Dff T0 (%) | | 103 | 106 | 101 |
| protease activity (USP units/cps) | 1,250-3,850 USP units/cps | 1,984 | 2,240 | 2,048 | 1,984 |
| amylase activity (USP units/cps) | 1,600-6,575 USP units/cps | 2,496 | 2,688 | 2,880 | 2,688 |
| Pthalic Acid(%) | NMT 1.4% | 0.1 | 0.1 | 0.1 | 0.1 |
| LoD (%) | NMT 5.0% | 1.6 | 0.5 | 0.2 | 0.3 |
| dissolution (%) | NLT 75% 30 min | 84% (RSD 2.0) | 91% (RSD 2.6) | 87% (RSD 3.7) | 84% RD 1.4) |
| dissolution (%) × 1.125 | | 94% (RSD 2.3) | 103% (RSD 2.7) | 98% (RSD 4.0) | 94% (RSD 1.7) |
| Weight n = 10 (mg) | | 64 | 64 | 64 | 64 |

TABLE 17

Analysis of enterically coated diluted pancrelipase microtablets μT3 (carrier: microcrystalline cellulose B and trehalose); storage conditions: 25° C., 60% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 746 | 770 | 779 | 792 |
| | % label claim | 99 | 104 | 104 | 106 |
| | Dff T0 (%) | | 104 | 104 | 106 |
| protease activity (USP units/cps) | 1,250-3,850 USP units/cps | 1,980 | 2,112 | 2,112 | 2,112 |
| amylase activity (USP units/cps) | 1,600-6,575 USP units/cps | 2,640 | 2,838 | 2,772 | 2,838 |
| Pthalic Acid(%) | NMT 1.4% | 0.1 | 0.1 | 0.1 | 0.1 |
| LoD (%) | NMT 5.0% | 1.6 | 0.5 | 0.2 | 0.3 |
| dissolution (%) | NLT 75% 30 min | 87% (RSD 2.4) | 91% (RSD 2.6) | 89% (RSD 1.4) | 91% RD 3.4) |
| dissolution (%) × 1.125 | | 98% (RSD 2.1) | 102% (RSD 2.7) | 100% (RSD 1.2) | 103% (RSD 3.4) |
| Weight n = 10 (mg) | | 66 | 66 | 66 | 66 |

TABLE 18

Analysis of enterically coated diluted pancrelipase microtablets μT3 (carrier: microcrystalline cellulose B and trehalose); storage conditions: 40° C., 75% relative humidity

| Test | Specification | Time 0 | Time 1 mo | Time 2 mo | Time 3 mo |
|---|---|---|---|---|---|
| Appearance | Light small brown beads | corresp | corresp | corresp | corresp |
| lipase activity (USP units/cps) | 90-110% of label claim 675-825 USP units/cps | 746 | 766 | 766 | 766 |
| | % label claim | 99 | 102 | 102 | 102 |
| | Dff T0 (%) | | 103 | 103 | 103 |
| protease activity (USP units/cps) | 1,250-3,850USP units/cps | 1,980 | 1,980 | 2,046 | 2,046 |
| amylase activity (USP units/cps) | 1,600-6,575 USP units/cps | 2,640 | 2,838 | 2,706 | 2,904 |
| Pthalic Acid(%) | NMT 1.4% | 0.1 | 0.1 | 0.1 | 0.1 |
| LoD (%) | NMT 5.0% | 1.6 | 0.4 | 0.1 | 0.3 |
| dissolution (%) | NLT 75% 30 min | 87% (RSD 2.4) | 89% (RSD 1.0) | 86% (RSD 1.4) | 88% RD 2.4) |
| dissolution (%) × 1.125 | | 98% (RSD 2.1) | 100% (RSD 0.9) | 97% (RSD 1.2) | 99% (RSD 2.1) |
| Weight n = 10 (mg) | | 66 | 66 | 66 | 66 |

The results indicate that the diluted pancrelipase of the invention are highly stable for long period of time even under aggravated conditions of storage.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

We claim:

1. A pharmaceutical composition comprising a blend of at least one digestive enzyme and at least one carrier, wherein a total amount of the at least one digestive enzyme in the pharmaceutical composition is from 4% to 19% by weight, and the at least one carrier comprises microcrystalline cellulose having an average particle size greater than 100 μm.

2. The pharmaceutical composition of claim 1, wherein the at least one digestive enzyme is in the form of enterically coated pancrelipase beads.

3. The pharmaceutical composition of claim 2, wherein the total amount of the at least one digestive enzyme in the pharmaceutical composition is from 10% to 15% by weight.

4. The pharmaceutical composition of claim 2, wherein the enterically coated pancrelipase beads comprise from 4 wt. % to 19 wt. % of pancrelipase based on a total weight of uncoated beads and from 70 wt. % to 96 wt. % of the at least one carrier based on the total weight of the uncoated beads.

5. The pharmaceutical composition of claim 2, wherein the enterically coated pancrelipase beads comprise from 10 wt. % to 15 wt. % of pancrelipase based on a total weight of uncoated beads and from 75 wt. % to 90 wt. % of the at least one carrier based on the total weight of the uncoated beads.

6. The pharmaceutical composition of claim 2, wherein the enterically coated pancrelipase beads comprise from 10 wt. % to 15 wt. % of pancrelipase based on a total weight of uncoated beads and from 80 wt. % to 85 wt. % of the at least one carrier based on the total weight of the uncoated beads.

7. The pharmaceutical composition of claim 2, wherein the enterically coated pancrelipase beads comprise 15 wt. % of pancrelipase based on a total weight of uncoated beads, 80 wt. % of the at least one carrier based on the total weight of the uncoated beads, and 5 wt. % of further excipients based on the total weight of the uncoated beads.

8. The pharmaceutical composition of claim 2, wherein the enterically coated pancrelipase beads comprise 10 wt. % of pancrelipase based on a total weight of uncoated beads, 85 wt. % of the at least one carrier based on the total weight of the uncoated beads, and 5 wt. % of further excipients, based on the total weight of the uncoated beads.

9. The pharmaceutical composition of claim 1, wherein the at least one carrier comprises the microcrystalline cellulose having a moisture content equal or less than 5%, a nominal mean particle size of 160 μm, mesh size 38: amount retained ≤1.0%, mesh size 94: amount retained ≤50.0%, and mesh size 300: amount retained ≤70.0%.

10. The pharmaceutical composition of claim 1, wherein the at least one carrier comprises the microcrystalline cellulose having a moisture content equal to or less than 5%, a nominal mean particle size of 180 μm, mesh size 60: amount retained ≤10.0%, and mesh size 100: amount retained ≤50.0%.

11. The pharmaceutical composition of claim 1, wherein the at least one carrier comprises a first microcrystalline cellulose having a moisture content equal to or less than 5%, a nominal mean particle size of 160 μm, mesh size 38: amount retained ≤1.0%, mesh size 94: amount retained ≤50.0%, and mesh size 300: amount retained ≤70.0%, and a second microcrystalline cellulose having a moisture content equal to or less than 5%, a nominal mean particle size of 50 μm, mesh size 60: amount retained ≤1.0%, and mesh size 200: amount retained 30.0%, and a weight ratio of the first and second microcrystalline cellulose is 16:1.

12. The pharmaceutical composition of claim 1, wherein the at least one carrier comprises a mixture of the microcrystalline cellulose and trehalose.

13. The pharmaceutical composition of claim 12, wherein the at least one carrier comprises the microcrystalline cellulose having a moisture content equal to or less than 5%, a nominal mean particle size of 160 μm, mesh size 38: amount retained ≤1.0%, a mesh size 94: amount retained ≤50.0%, and mesh size 300: amount retained ≤70.0% and trehalose, and a weight ratio of the microcrystalline cellulose and the trehalose is 1:1.

14. The pharmaceutical composition of claim 1, wherein the at least one carrier comprises the microcrystalline cellulose having a moisture content equal to or less than 5%, a nominal mean particle size of 180 μm, mesh size 60: amount retained ≤10.0%, mesh size 100: amount retained ≤50.0%, and trehalose, and a weight ratio of the microcrystalline cellulose and the trehalose is 1:1.

15. A dosage form comprising the pharmaceutical composition of claim 1.

16. The dosage form of claim 15, wherein the dosage form is a capsule.

17. The dosage form of claim 16, wherein the at least one digestive enzyme is lipase from 500 to 5000 USP units.

18. The dosage form of claim 17, wherein the at least one digestive enzyme is lipase from 675 to 825 USP units.

19. The dosage form of claim 15, wherein the at least one digestive enzyme comprises lipase from 675 to 825 USP units, protease from 1,250 to 3,850 USP units, and amylase from 1,600 to 6,575 USP units.

20. A package comprising a sealed container, wherein the sealed container comprises a moisture resistant material, a desiccant, and at least one dosage form of claim 15, and the desiccant and at least one dosage form are inside the sealed container.

21. The package of claim 20, wherein the moisture resistant material is selected from the group consisting of metal, glass, plastic, metal coated plastic, and mixtures thereof.

22. The package of claim 20, wherein the desiccant is selected from the group consisting of molecular sieves, clay, silica gel, activated carbon, and combinations thereof.

23. The dosage form of claim 15, wherein the dosage form has a residual moisture content below 5%.

24. The dosage form of claim 15, wherein the dosage form has a residual moisture content below 2%.

25. The pharmaceutical composition of claim 2, wherein the enterically coated pancrelipase beads comprise an enteric coating comprising an enteric polymer comprising 4% to 10% of talc based on a total weight of the enterically coated pancrelipase beads.

26. The pharmaceutical composition of claim 1, wherein the pharmaceutical composition exhibits a loss of enzymatic activity of no more than 25% after six months of accelerated stability testing.

27. The dosage form of claim 15, wherein the dosage form exhibits a loss of enzymatic activity of no more than 25% after six months of accelerated stability testing.

* * * * *